United States Patent
Hynes et al.

(10) Patent No.: US 11,597,769 B2
(45) Date of Patent: Mar. 7, 2023

(54) NANOBODY BASED IMAGING AND TARGETING OF ECM IN DISEASE AND DEVELOPMENT

(71) Applicants: Massachusetts Institute of Technology, Cambridge, MA (US); Children's Medical Center Corporation, Boston, MA (US); Whitehead Institute for Biomedical Research, Cambridge, MA (US)

(72) Inventors: Richard O. Hynes, Winchester, MA (US); Noor Jailkhani, Cambridge, MA (US); Hidde L. Ploegh, Boston, MA (US); Yushu Joy Xie, Brookline, MA (US)

(73) Assignees: Massachusetts Institute of Technology, Cambridge, MA (US); Children's Medical Center Corporation, Boston, MA (US); Whitehead Institute for Biomedical Research, Cambridge, MA (US)

( * ) Notice: Subject to any disclaimer, the term of this patent is extended or adjusted under 35 U.S.C. 154(b) by 855 days.

(21) Appl. No.: 16/258,457

(22) Filed: Jan. 25, 2019

(65) Prior Publication Data

US 2019/0225693 A1 Jul. 25, 2019

Related U.S. Application Data

(60) Provisional application No. 62/621,811, filed on Jan. 25, 2018.

(51) Int. Cl.
*C07K 16/28* (2006.01)
*A61P 35/04* (2006.01)
*A61K 47/68* (2017.01)
*A61K 49/08* (2006.01)
*A61K 49/00* (2006.01)
*A61K 51/10* (2006.01)
*C07K 14/78* (2006.01)
*C07K 16/18* (2006.01)
*B82Y 5/00* (2011.01)
*A61K 39/00* (2006.01)

(52) U.S. Cl.
CPC ...... *C07K 16/2842* (2013.01); *A61K 47/6809* (2017.08); *A61K 47/6813* (2017.08); *A61K 47/6849* (2017.08); *A61K 47/6851* (2017.08); *A61K 49/0058* (2013.01); *A61K 49/085* (2013.01); *A61K 51/1027* (2013.01); *A61K 51/1045* (2013.01); *A61K 51/1051* (2013.01); *A61K 51/1057* (2013.01); *A61K 51/1093* (2013.01); *A61P 35/04* (2018.01); *C07K 14/78* (2013.01); *C07K 16/18* (2013.01); *A61K 2039/505* (2013.01); *B82Y 5/00* (2013.01); *C07K 2317/22* (2013.01); *C07K 2317/569* (2013.01); *C07K 2319/03* (2013.01); *C07K 2319/33* (2013.01)

(58) Field of Classification Search
CPC .... C07K 16/2842; C07K 14/78; C07K 16/18; C07K 2317/22; C07K 2317/569; C07K 2319/03; C07K 2319/33; C07K 14/7051; C07K 16/005; C07K 16/462; C07K 2319/00; A61K 47/6809; A61K 47/6813; A61K 47/6849; A61K 47/6851; A61K 49/0058; A61K 49/085; A61K 51/1027; A61K 51/1045; A61K 51/1051; A61K 51/1057; A61K 51/1093; A61K 2039/505; A61K 2039/5156; A61K 2039/5158; A61K 39/0011; A61K 47/6843; A61K 51/1018; A61K 38/1741; A61K 47/6425; A61P 35/04; A61P 35/00; B82Y 5/00; C12N 2500/10; C12N 2533/90; C12N 15/1037; C12N 2501/515; C12N 5/0636

See application file for complete search history.

(56) References Cited

U.S. PATENT DOCUMENTS

2011/0294982 A1* 12/2011 Vanlandschoot .. C07K 16/2842
530/350
2013/0136744 A1 5/2013 Bouche et al.

FOREIGN PATENT DOCUMENTS

WO WO-0076456 A2 * 12/2000 ............. C07K 14/78
WO WO 2014/145252 A2 9/2014
WO WO 2017/194782 A2 11/2017

OTHER PUBLICATIONS

Peterson et al., Generating Single-Domain Antibodies Against Fibronectin Splice Variants, Thesis. (Year: 2017).*
Lloyd et al., Protein Engineering, Design & Selection 22:159-168 (Year: 2009).*
Edwards et al., J Mol Biol. 334(1): 103-118 (Year: 2003).*
Nguyen et al., EMBO Journal, 19(5): 921-930 (Year: 2000).*

(Continued)

*Primary Examiner* — Phuong Huynh
(74) *Attorney, Agent, or Firm* — Wolf, Greenfield & Sacks, P.C.

(57) ABSTRACT

Methods for developing disease-related nanobodies and related products and kits are provided. The disease-specific proteins are extracellular matrix (ECM) proteins, domains or epitopes that are associated with various aspects of disease and are not present, or are present in very low quantities, in non-diseased individuals. Highly effective nanobodies capable of specifically binding to these ECM protein epitopes useful in in vivo imaging assays, the detection, diagnosis and treatment of diseases as well as monitoring therapeutic progress in a patient with a disease are provided herein.

15 Claims, 13 Drawing Sheets
Specification includes a Sequence Listing.

(56) References Cited

OTHER PUBLICATIONS

Extended European Search Report for EP 19743635.5 dated Oct. 6, 2021.
International Search Report and Written Opinion for PCT/US2019/015290 dated Apr. 5, 2019.
International Preliminary Report on Patentability for PCT/US2019/015290 dated Aug. 6, 2020.
Cortez-Retamozo et al., Efficient cancer therapy with a nanobody-based conjugate. Cancer Res. Apr. 15, 2004;64(8):2853-7. doi: 10.1158/0008-5472.can-03-3935. PMID: 15087403.
Hassanzadeh-Ghassabeh et al., Nanobodies and their potential applications. Nanomedicine (Lond). Jun. 2013;8(6):1013-26. doi: 10.2217/nnm.13.86. PMID: 23730699.
Kaspar et al., Fibronectin as target for tumor therapy. Int J Cancer. Mar. 15, 2006;118(6):1331-9. doi: 10.1002/ijc.21677. PMID: 16381025.
Narunsky et al., Imaging aspects of the tumor stroma with therapeutic implications. Pharmacol Ther. Feb. 2014;141(2):192-208. doi: 10.1016/j.pharmthera.2013.10.003. Epub Oct. 14, 2013. PMID: 24134903; PMCID: PMC3947248.
Pardon et al., A general protocol for the generation of Nanobodies for structural biology. Nat Protoc. Mar. 2014;9(3):674-93. doi: 10.1038/nprot.2014.039. Epub Feb. 27, 2014. PMID: 24577359; PMCID: PMC4297639.
Sadelain et al., The basic principles of chimeric antigen receptor design. Cancer Discov. Apr. 2013;3(4):388-98. doi: 10.1158/2159-8290.CD-12-0548. Epub Apr. 2, 2013. PMID: 23550147; PMCID: PMC3667586.
[No Author Listed], MIT Catalog Library Record showing May 9, 2017 catalog date for Peterson et al., Generating Single-Domain Antibodies Against Fibronectin Splice Variants, Thesis (Year: 2017).
Giblin et al., Tenascin-C: Form versus function. Cell Adh Migr. 2015;9(1-2):48-82. doi: 10.4161/19336918.2014.987587. PMID: 25482829; PMCID: PMC4422809.
Hynes, Molecular biology of fibronectin. Annu Rev Cell Biol. 1985;1:67-90. doi: 10.1146/annurev.cb.01.110185.000435. PMID: 3916323.
Naba et al., The matrisome: in silico definition and in vivo characterization by proteomics of normal and tumor extracellular matrices. Mol Cell Proteomics. Apr. 2012;11(4):M111.014647. doi: 10.1074/mcp.M111.014647. Epub Dec. 9, 2011. PMID: 22159717; PMCID: PMC3322572.
White et al., Fibronectin splice variants: understanding their multiple roles in health and disease using engineered mouse models. IUBMB Life. Jul. 2011;63(7):538-46. doi: 10.1002/iub.493. PMID: 21698758.

\* cited by examiner

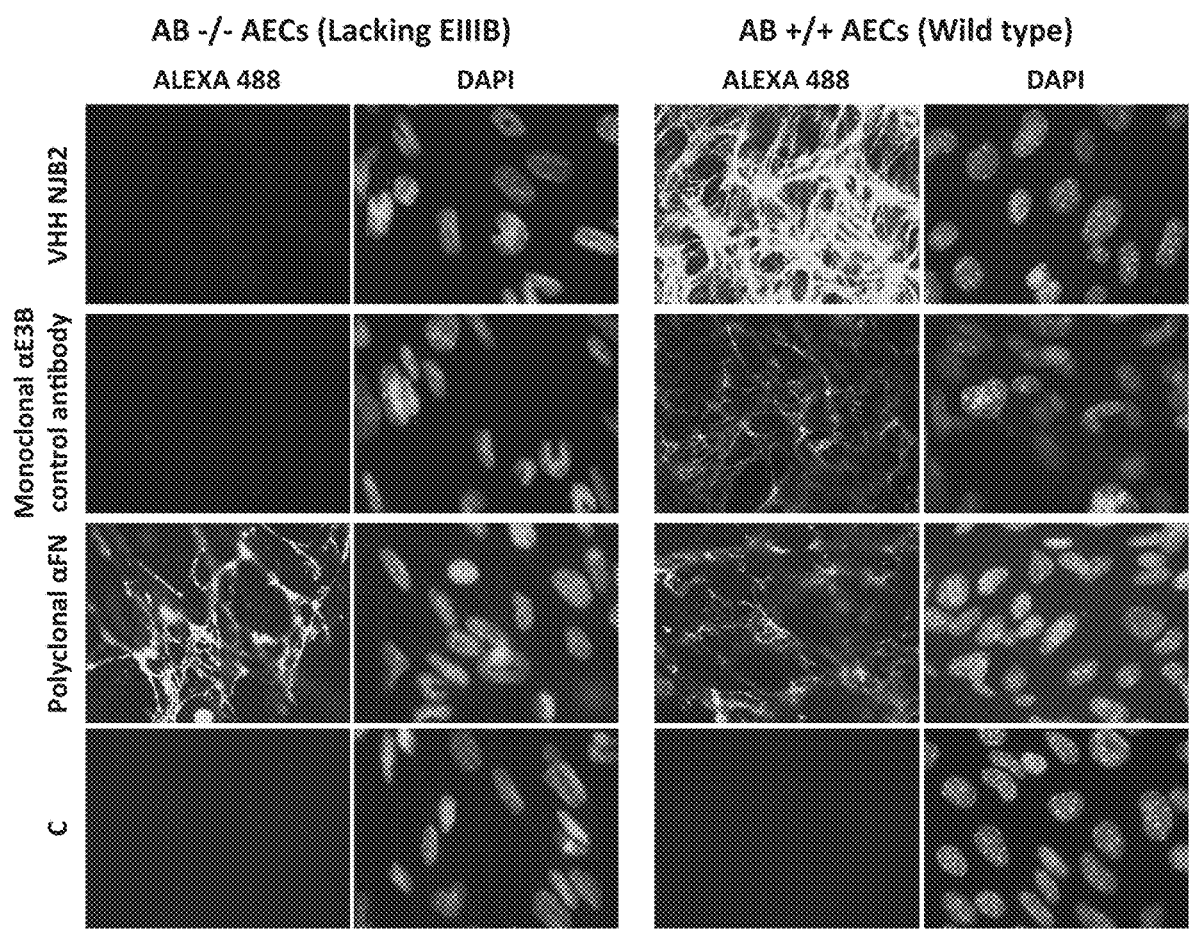

Primary tumor    Lung metastases $^{18}$FDG-PET/CT    $^{64}$Cu-NJB2 IMMUNO-PET/CT $^{18}$FDG-PET/CT $^{64}$Cu-NJB2 PET/CT $^{18}$FDG-PET/CT $^{64}$Cu-NJB2 PET/CT Percentage of patients positive for EIIIB: 44%

Control TNC antibody signal ~2

Fig.13
NJT3-Texas red
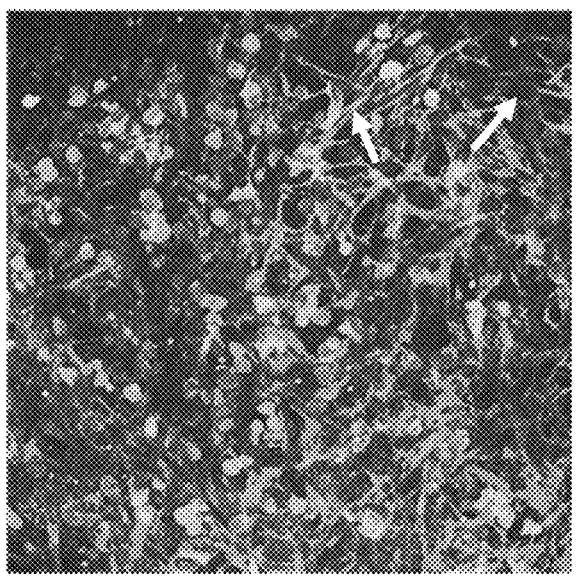
NJT4-Texas red
NJT6-Texas red
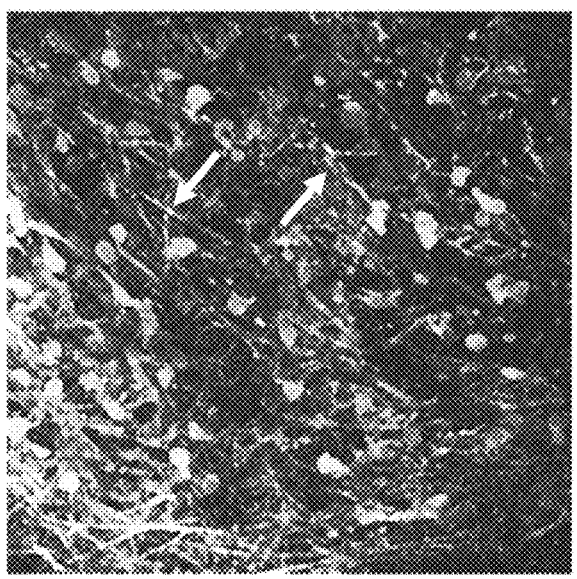

NANOBODY BASED IMAGING AND TARGETING OF ECM IN DISEASE AND DEVELOPMENT

RELATED APPLICATION

This application claims the benefit of the filing date under 35 U.S.C. § 119 of U.S. Provisional Application Ser. No. 62/621,811, filed Jan. 25, 2018, the entire contents of which are incorporated by reference herein.

FEDERALLY SPONSORED RESEARCH

This invention was made with Government support under Grant No. W81XWH-14-1-0240 awarded by the U.S. Army Medical Research and Material Command. The Government has certain rights in the invention.

FIELD OF THE INVENTION

The invention relates in some aspects to generating and identifying nanobodies specific for diseased state extracellular matrix (ECM) proteins and the use of such nanobodies for diagnostic, prognostic, and therapeutic purposes, as well as associated reagents, products and kits.

BACKGROUND OF THE INVENTION

The extracellular matrix (ECM) and ECM proteins play important physiological roles in growth, wound healing, cell migration, and differentiation, among other processes. Furthermore, in diseased states, the composition of the ECM changes and prior observations indicate that these changes in extracellular matrix (ECM) proteins can play significant roles in cancer progression and metastasis, in cardiovascular diseases and in fibrosis. The field of proteomics involves the study of proteins in complex physiological systems and their role in these systems. Large data sets have been generated using genomic and proteomic methods, but the use of that information to identify the role of extracellular matrix (ECM) proteins in disease has been limited. This is because the ECM is insoluble and crosslinked and its composition has been difficult to determine until recent application of proteomics targeted specifically to ECM proteins.

SUMMARY OF INVENTION

This invention covers methods for development, isolation and use of nanobodies (i.e., single-domain antibodies from alpacas) to ECM proteins for use in imaging and targeting disease states. The ECM epitopes of interest are specifically expressed in cancer, metastasis and other disease states. These nanobodies may be used for a variety of purposes such as to target the ECM of tumors, metastases or other disease loci and using the specificity of the nanobodies to deliver [1] imaging agents; [2] therapeutic agents of diverse types; [3] immune-modulators, including modified T cells; or [4] use the functional properties of the nanobodies themselves to affect the disease state.

The invention also involves methods for producing the nanobodies by immunizing camelids with tumor-enriched ECM proteins and/or domains (collectively, ECM epitopes) that have been defined by prior proteomic analyses of tumors and metastases. Libraries generated using these methods provide a renewable source of anti-ECM antibodies to other tumor-enhanced ECM epitopes for the generation of additional tumor-selective anti-ECM nanobodies targeting metastasis and other diseased states.

Aspects of the disclosure relate to compositions, comprising nanobodies which are specific for and bind directly to a diseased state extracellular matrix (ECM) epitope, wherein the diseased state ECM epitope that is present in greater amounts in a diseased tissue than in a normal tissue, and wherein the nanobody is conjugated to one or more active agents.

In some embodiments, the active agent is linked to the N-terminus of the nanobody. In other embodiments, the active agent is linked to the C-terminus of the nanobody. In one embodiment, the active agent is an imaging probe. In some embodiments, the imaging probe is selected from fluorophores, PET tracers, SPECT, NIR, Magnetic particle imaging, or radio-isotopes. In other embodiments, the active agent is selected from drugs, toxins, cytokines, immuno-modulators, ECM remodeling enzymes, siRNAs, shRNAs, nanoparticles, CAR-T cells or radioisotopes for targeted therapies.

In some embodiments, the nanobody once administered to a subject, binds specifically to the diseased state ECM protein epitope with a binding affinity sufficient to concentrate the nanobody and any attached active agent in the region of the tumor or other disease locus such that the level at the disease site is much higher than that elsewhere in the body. The affinities of nanobodies are in the nM to sub-pM range (i.e. of antibodies tested in the examples NJB2 has an affinity of ~4 nM by BLI and the NJT3, NJT4 and NJT6 have sub-pM affinities based on BLI), which is demonstrably sufficient to achieve this goal, and is similar to the affinities of conventional antibodies in therapeutic use (e.g., rituxan, herceptin). Nanobody affinity can be determined experimentally.

In some embodiments, the diseased state ECM epitope is an epitope in EIIIA or EIIIB domain of fibronectin. In other embodiments, the diseased state ECM epitope is tenascin C or an epitope of tenascin C. In one embodiment, the nanobody comprises a sequence set forth in SEQ ID NOs: 1-4 or modifications made to such sequences to improve their affinity or efficacy.

Other aspects of the disclosure relate to a composition, comprising a nanobody comprising one of the sequences set forth in SEQ ID NOs: 1-4 or derivatives with minor differences in sequence, formulated in a pharmaceutically acceptable carrier. In some embodiments, the nanobody is conjugated to an active agent. In other embodiments, the nanobody is incorporated into or conjugated with a monoclonal antibody, a humanized antibody, a chimeric antibody, a human antibody, or an antibody fragment or another protein such as a chimeric antigen receptor allowing targeting of additional epitopes.

Another aspect of the disclosure includes a method comprising administering to a subject having a tumor, or other disease state, a composition described herein, in an effective amount to deliver the active agent to the tumor/site of disease. In some embodiments, the method involves determining the presence or absence of one or more ECM proteins or epitopes characteristic of a diseased state in a subject and determining whether and where in the body the subject has disease. In such embodiments, the presence or absence of one or more ECM proteins or epitopes is determined by immunohistochemistry or immunofluorescence or other imaging modalities such as noninvasive in vivo imaging modalities such as Immuno-PET/CT.

In another embodiment, the method is a method of tracking over time the progression of a disease to an advanced stage by assessing the presence, amount or absence of one or more ECM proteins or epitopes characteristic of a diseased state. In one embodiment, the method is a method for measuring the presence, amount or absence of one or more ECM proteins or epitopes associated with a diseased state in a tissue sample isolated from a subject at a first time point and a second time point and determining the progression of the disease to a more advanced stage based on changes in the presence, amount or absence of one or more ECM epitopes associated with a diseased state at the first and second time points. In some embodiments, the diseased state is a cancer, atherosclerosis, myocardial infarction, fibrosis, chronic inflammation or a wound. In one embodiment, the cancer is a metastatic cancer.

In some embodiments, when the ECM epitopes associated with a diseased state are present at a higher level in the isolated tissue sample from the second time-point, the disease has progressed to a more advanced stage. In another embodiment, when the ECM epitopes associated with a diseased state are present at a lower level in the isolated tissue sample from the second time-point, the disease has regressed to a less advanced stage. In some embodiments, when the ECM epitopes associated with a diseased state are present at a higher level in the isolated tissue sample from the second time-point, the cancer has progressed to a metastatic cancer or has grown. In other embodiments, when the ECM epitopes associated with a diseased state are present at a lower level in the isolated tissue sample from the second time-point, the cancer has regressed to a less advanced malignant state.

In some embodiments, the ECM epitopes are detected using one or more nanobodies that specifically bind to the ECM epitopes. In one embodiment, the ECM proteins or epitopes are analyzed using a quantitative ELISA or Western blot. In some embodiments, the ECM epitopes are detected using a mass spectrometry method and/or a chromatographic method.

Another aspect of the disclosure includes a method of generating diverse libraries of nanobodies specific for ECM proteins and their epitopes, wherein the ECM preparation is ECM from one or more human cancer metastases enriched in metastasis-associated proteins. Such a library is derived by isolating lymphocytes from blood collected from a camelid which has been immunized with a complex ECM-enriched preparation, extracting lymphocyte RNA, and constructing an M13 phage-display-based nanobody library from the lymphocyte RNAs, wherein the library is a diverse and renewable library of ECM-specific nanobodies, from which one can isolate numerous specific anti-ECM nanobodies as needed.

In some embodiments, the camelid is an Alpaca. In another embodiment, nanobodies are isolated from the library and used as a scaffold for in vitro affinity maturation to further optimize binding to an ECM epitope.

A further aspect of the disclosure provides a library of nucleic acid vectors, comprising a plurality of vectors, each vector having a distinct DNA sequence within the vector, wherein each DNA sequence has at least 80% sequence identity with 1 or more other DNA sequences within the vectors, and wherein the library has a diversity of $10^5$ to $10^6$ cfu/ml and wherein each DNA sequence encodes a nanobody having the ability to bind to an ECM protein epitope of relevance to the disease state.

In some embodiments, the ECM epitope is a diseased state ECM epitope. In another embodiment, the diseased state ECM epitope is EIIIA or EIIIB domain of fibronectin. In other embodiments, the diseased state ECM epitope is tenascin C or an epitope of tenascin C. In one embodiment, the nanobody comprises a sequence having at least 70% sequence identity with a sequence of SEQ ID NOs: 1-4.

In some aspects, the disclosure is a method for generating a chimeric antigen receptor T-cell (CAR T cell), involving generating a chimeric antigen receptor (CAR) construct, having an ectodomain comprising a nanobody which is specific for and binds directly to a diseased-state extracellular matrix (ECM) epitope, wherein the diseased-state ECM epitope is present in greater amounts in a diseased tissue than in a normal tissue, a transmembrane domain, and an endodomain, transfecting T cells removed from blood of a subject, and expressing the CAR construct to produce a functional CAR in the T cells to produce a CAR T cell.

In other aspects, the disclosure provides a chimeric antigen receptor T-cell (CAR T cell) having an ectodomain comprising a nanobody which is specific for and binds directly to a diseased-state extracellular matrix (ECM) epitope, wherein the diseased-state ECM epitope is present in greater amounts in a diseased tissue than in a normal tissue, a transmembrane domain, and an endodomain.

In another aspect, the disclosure provides a chimeric antigen receptor (CAR) construct including a nucleic acid encoding a CAR having an ectodomain comprising a nanobody which is specific for and binds directly to a diseased-state extracellular matrix (ECM) epitope, wherein the diseased-state ECM epitope is present in greater amounts in a diseased tissue than in a normal tissue, a transmembrane domain, and an endodomain.

In some embodiments, the nanobody specifically binds the diseased-state ECM epitope with a binding affinity in the nM to sub-pM range, as measured by Bilayer Interferometry (BLI) or other methods.

In some embodiments, the diseased-state ECM epitope is an epitope in EIIIA or EIIIB domain of fibronectin. In other embodiments, the diseased state ECM protein is Tenascin C or an epitope of tenascin C. In other embodiments, the nanobody comprises a sequence set forth in SEQ ID NOs: 1-4 or modifications made to such sequences to improve their affinity or efficacy.

In other aspects, the disclosure provides a chimeric antigen receptor (CAR) construct including a nucleic acid encoding a CAR having an ectodomain comprised of a peptide comprising a sequence set forth in SEQ ID NOs: 1-4 or fragment thereof which is specific for and binds directly to a diseased-state extracellular matrix (ECM) epitope, wherein the diseased-state ECM epitope is present in greater amounts in a diseased tissue than in a normal tissue, a transmembrane domain, and an endodomain.

In some embodiments, the peptide is a monoclonal antibody, a humanized antibody, a chimeric antibody, a human antibody, or an antibody fragment. In another embodiment, the fragment is a CDR.

In some embodiments, the peptide specifically binds the diseased-state ECM epitope with a binding affinity in the nM to sub-pM range, as measured by Bilayer Interferometry (BLI) or other methods. In some embodiments, the diseased-state ECM epitope is an epitope in EIIIA or EIIIB domain of fibronectin. In other embodiments, the diseased-state ECM protein is Tenascin C or an epitope of tenascin C. In another embodiment, the peptide targets an epitope expressed by a diseased-state exon within a variably spliced ECM protein.

Further aspects of the disclosure provide a method for treating a subject having a solid tumor, including administering to the subject having the solid tumor a chimeric antigen receptor T-cell (CAR T cell), wherein the CAR T cell comprises a T cell having a chimeric antigen receptor (CAR)

construct, having an ectodomain comprised of a nanobody peptide comprising a sequence set forth in SEQ ID NOs: 1-4 or fragment thereof which is specific for and binds directly to a diseased-state extracellular matrix (ECM) epitope, wherein the diseased-state ECM epitope is present in greater amounts in a diseased tissue than in a normal tissue, a transmembrane domain, and an endodomain, in an effective amount to treat the subject having the solid tumor.

In some embodiments, the peptide is a monoclonal antibody, a humanized antibody, a chimeric antibody, a human antibody, or an antibody fragment. In some embodiment, the peptide is a nanobody. In another embodiment, the fragment is a CDR.

In some embodiments, the peptide specifically binds the diseased-state ECM epitope with a binding affinity in the nM to sub-pM range, as measured by Bilayer Interferometry (BLI) or other methods. In some embodiments, diseased-state ECM epitope is an epitope in EIIIA or EIIIB domain of fibronectin. In other embodiments, the diseased-state ECM protein is Tenascin C or an epitope of tenascin C. In another embodiment, the peptide targets an epitope expressed by a diseased state exon within a variably spliced ECM protein.

In some embodiments, the CAR is expressed in a T cell. In another embodiment, the CAR is expressed in a NK cell.

A futher aspect of the disclosure provides a method for recruiting immune cells to a solid tumor in a subject, involving administering to the subject having the solid tumor a chimeric antigen receptor T-cell (CAR T cell) or a chimeric antigen receptor NK-cell (CAR-NK cell), wherein the CAR T or CAR-NK cell comprises a T cell or NK cell having a chimeric antigen receptor (CAR) construct, having an ectodomain comprising a nanobody peptide comprising a sequence set forth in SEQ ID NOs: 1-4 or fragment thereof which is specific for and binds directly to a diseased state extracellular matrix (ECM) epitope, wherein the diseased-state ECM epitope is present in greater amounts in a diseased tissue than in a normal tissue, a transmembrane domain, and an endodomain, in an effective amount to recruit immune cells to the solid tumor.

In some embodiments, the peptide is a monoclonal antibody, a humanized antibody, a chimeric antibody, a human antibody, or an antibody fragment. In some embodiments, the peptide is a nanobody. In another embodiment, the fragment is a CDR.

In some embodiments, the peptide specifically binds the diseased-state ECM epitope with a binding affinity in the nM to sub-pM range, as measured by Bilayer Interferometry (BLI) or other methods. In some embodiments, the diseased-state ECM epitope is an epitope in EIIIA or EIIIB domain of fibronectin. In other embodiments, the diseased state ECM protein is Tenascin C or an epitope of tenascin C. In another embodiment, the peptide targets an epitope expressed by a diseased-state exon within a variably spliced ECM protein.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

FIGS. 1A-1B show ClustalW-based alignment of αEIIIB VHH sequences (FIG. 1A) and αTNC VHH sequences (FIG. 1B) each isolated from 2 rounds of Bio-panning. Differences in the complementarity-determining region, CDR3, or elsewhere in the nanobody, distinguish among the different nanobodies. CDR is a complementarity-determining region. Top to bottom, left to right the sequences in FIG. 1A correspond to SEQ ID NOs: 5, 1, 6, 7, 8, and 9. Top to bottom, left to right the sequences in FIG. 1B correspond to SEQ ID NOs: 10, 12, 11, 16, 3, 13, 14, 17, 15, 2, 4.

FIG. 2 shows that nanobody NJB2 specifically binds to an epitope in the EIIIB domain of fibronectin (FN). The NJB2 was site-specifically labelled with biotin via sortagging and detected with streptavidin-Alexa488. The right panel shows that VHH NJB2 specifically recognizes an epitope in the EIIIB domain of FN in the ECM of aortic endothelial cells derived from control/wild type mice. However, as shown in the left panel, NJB2 did not recognize FN in the ECM of endothelial cells derived from mice that lack the EIIIA and EIIIB domain of FN (AB null mice). The αEIIIB control was cells stained with mouse monoclonal IgG specific to an epitope in the EIIIB domain of FN. The negative control, C, was unstained cells.

FIG. 4A shows PET-CT images of a control NSG mouse (no tumor); PET signal was detected in kidney and bladder due to clearance of circulating nanobody. FIG. 4B shows NSG mice injected orthotopically (mammary fat pad) with LM2-TNBC cells. Labels were detected in kidney, bladder and primary tumor in the left lower mammary fat pad. FIG. 4C shows NSG mice injected via the tail vein (pulmonary metastasis model) with LM2-TNBC cells. PET signal was detected in kidney, bladder and metastases in the lungs. In these and all subsequent PET/CT images, the PET signal ($^{64}$Cu-coupled nanobody) appears the same color as the CT image; in the original color photos and, even more so, in the movies of 3-D reconstructions, the distinct images are clearly distinguishable and show extremely low background signal from the PET imaging (apart from the kidney and bladder signals).

5A) or with $^{64}$Cu-NJB2 (FIG. 5B) and imaged with PET/CT at 2 h post injection. LN Mets: Lymph Node Metastases. Liver Mets: Liver Metastases.

Figure 6A:
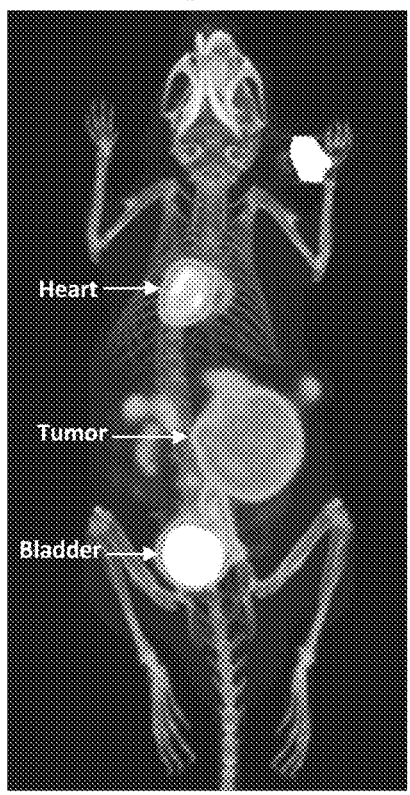
Figure 6B:
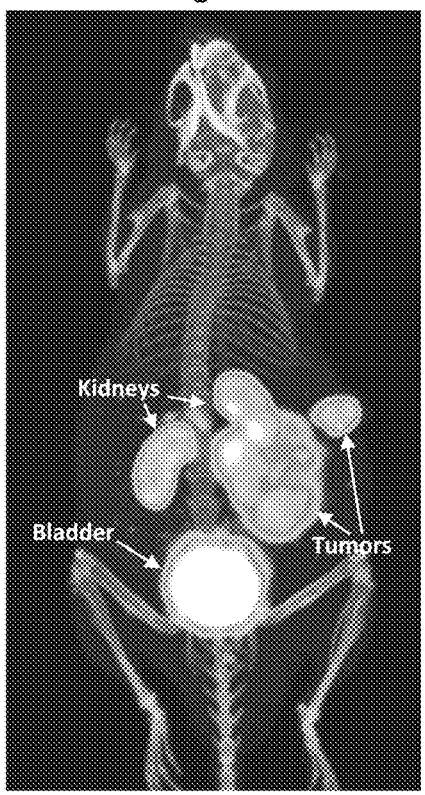
Figure 6C:
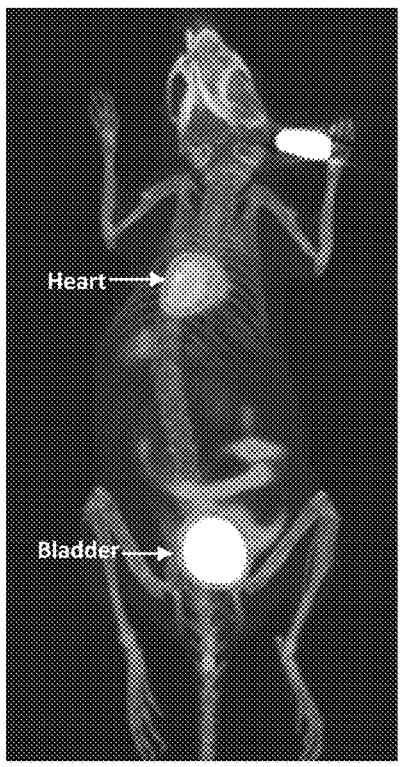
Figure 6D:
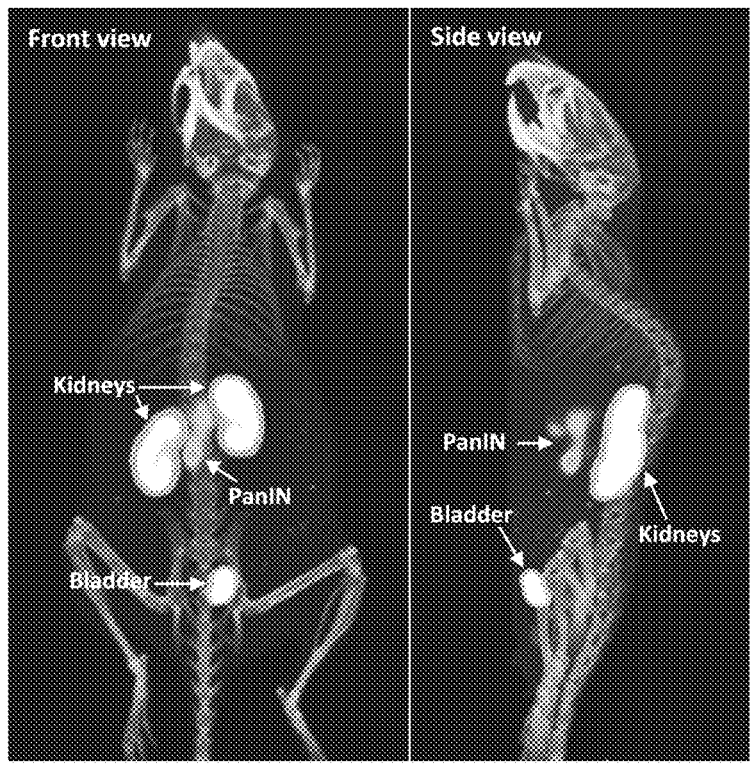

FIGS. 6A-6D show representative PET-CT images of mice with Pancreatic Ductal Adenocarcinoma or PDAC (top) and pancreatic intraepithelial neoplasia or PanINs (bottom) imaged with $^{18}$F-FDG (FIG. 6A, 6C) or $^{64}$Cu-NJB2 (FIG. 6B, 6D). In addition to the signal from clearance organs of kidneys and bladder, the nanobody signal was also seen from the PDAC tumors (FIG. 6B) and PanINs (FIG. 6D front and side view).

Figure 7A:
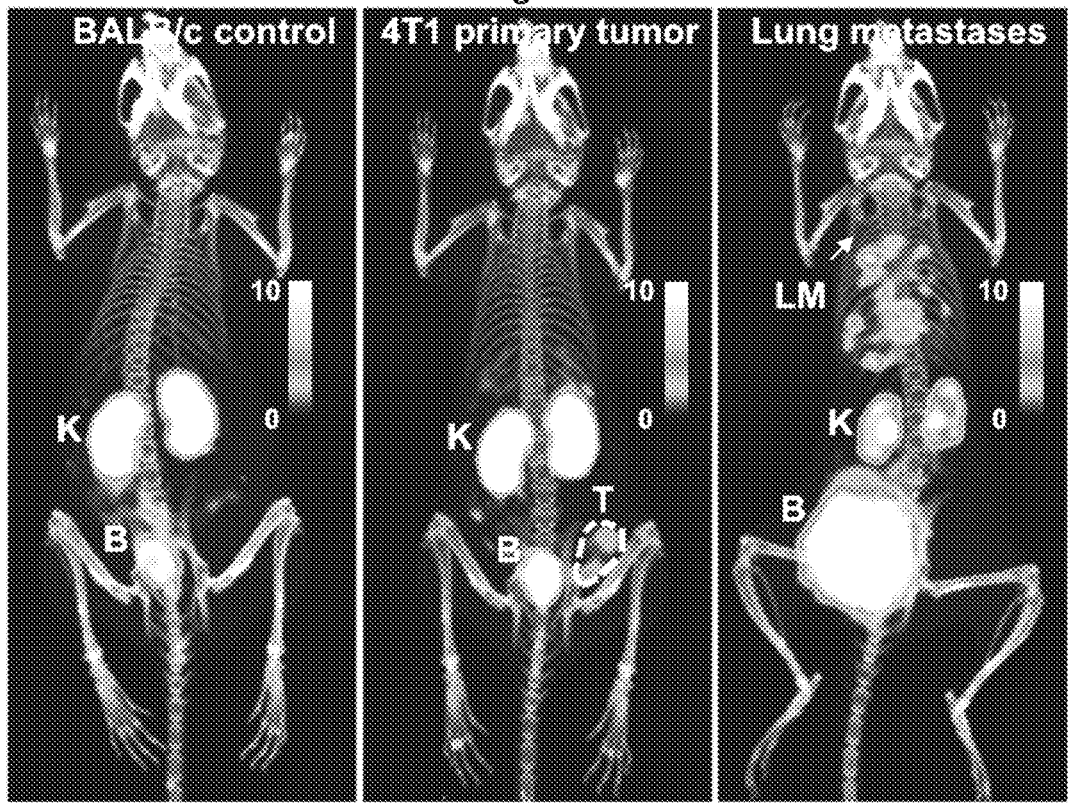
Figure 7B:
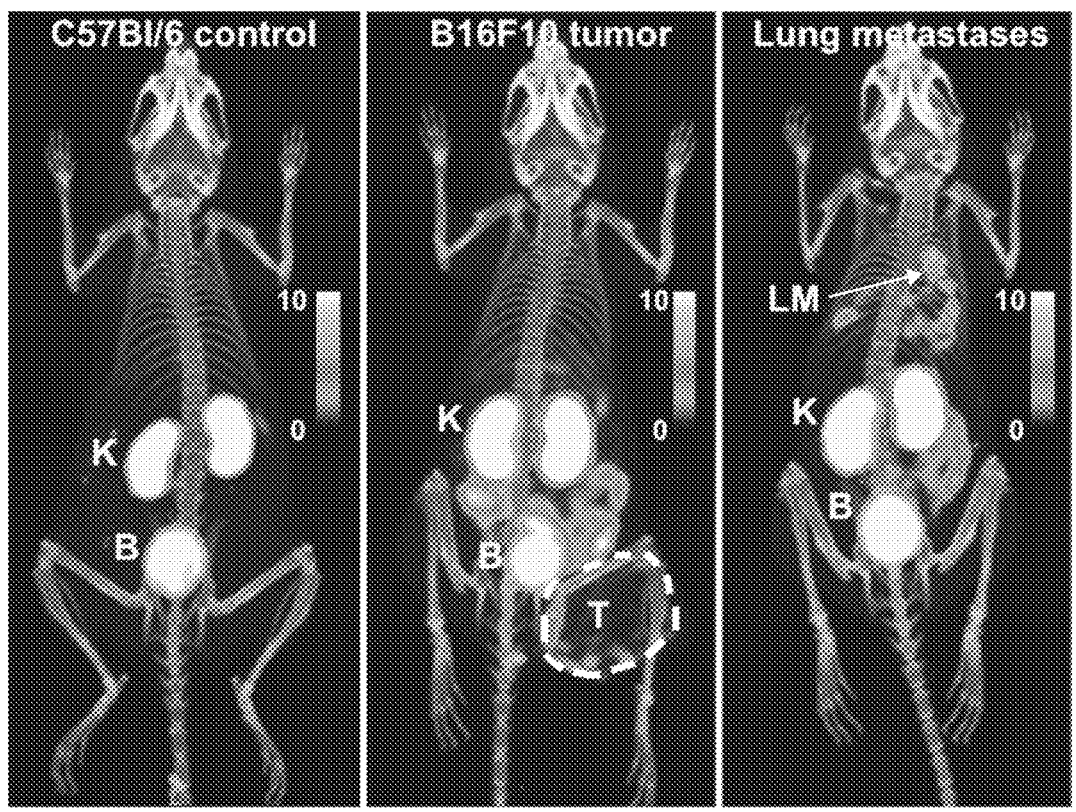

FIG. 7A shows control BALB/c mice and mice with primary tumors and lung metastases derived from 4T1 triple-negative breast cancer cells. FIG. 7B shows a control C57B1/6 mouse and mice with a subcutaneous tumor or lung metastases derived from B 16F10 melanoma cells. Representative PET/CT images show PET signals from the primary tumor "T", lung metastases "LM", kidneys "K" and bladder "B".

Figure 8:
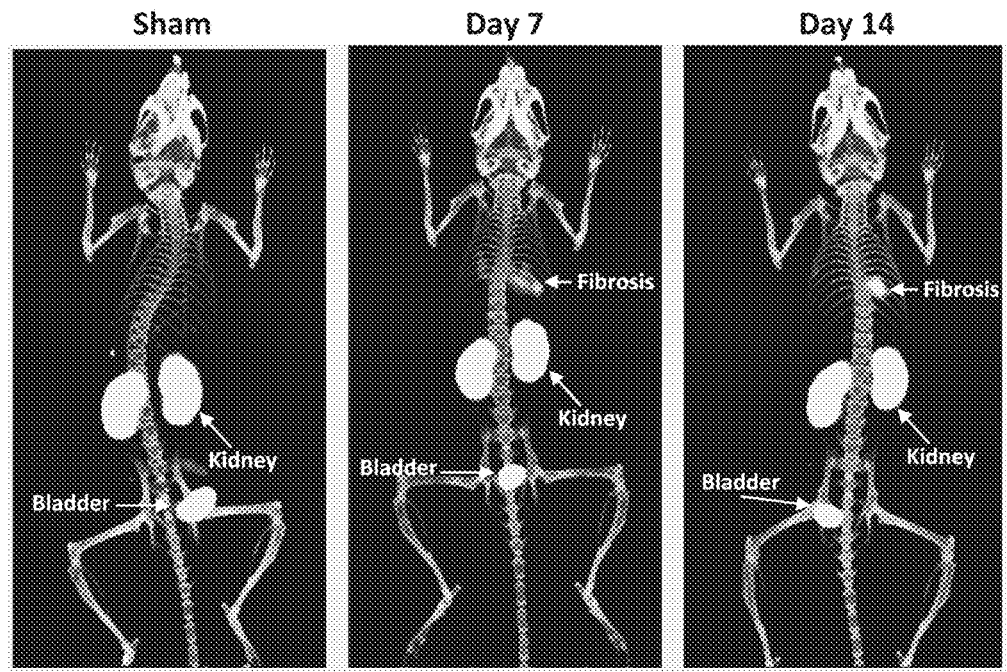

FIG. 8 shows pulmonary fibrosis induced by a single intra-tracheal administration of 0.035 U of bleomycin sulfate into C57BL/6 mice. Sham (saline) and bleomycin-treated mice (7 and 14 days after bleomycin administration) were imaged with $^{64}$Cu-NJB2 PET/CT. Representative PET/CT images of mice that were sham-treated, 7 days after bleomycin treatment and 14 days after bleomycin treatment. Fibrotic lesions (arrows) were visible in mice at both 7 and 14 days post bleomycin administration.

Figure 9:
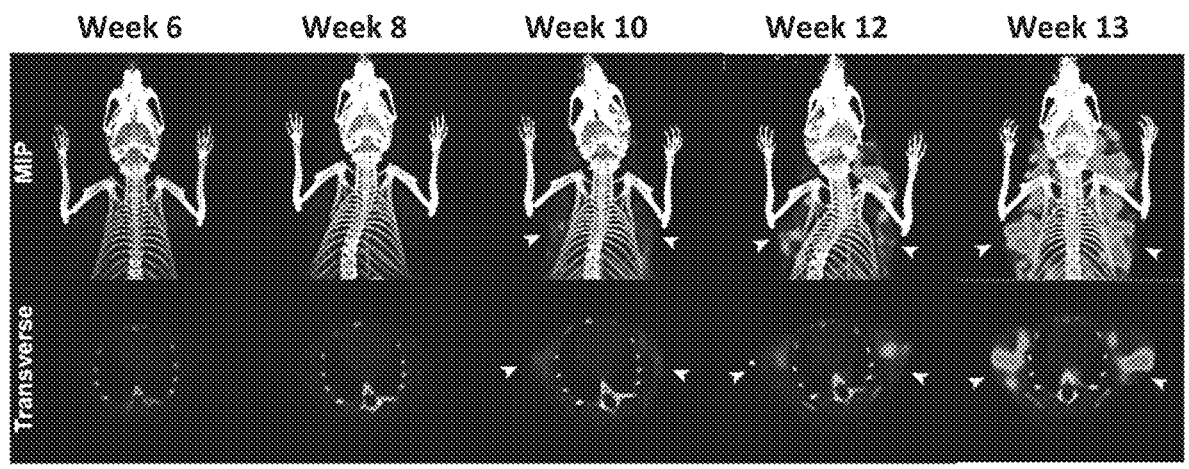

FIG. 9 shows representative PET/CT images of the upper body of MMTV-PyMT mice (n=7) imaged by $^{64}$Cu-NJB2 PET/CT at the ages of 6, 8, 10, 12 and 13 weeks. PET/CT signals from autochthonous mammary fat-pad tumors were visible from week 10 and onwards (arrowheads). Tumor progression in multiple mammary tumors was evident in all mice. Top panel shows maximum intensity projections (MIP) and bottom panel shows transverse sections.

Figure 10:
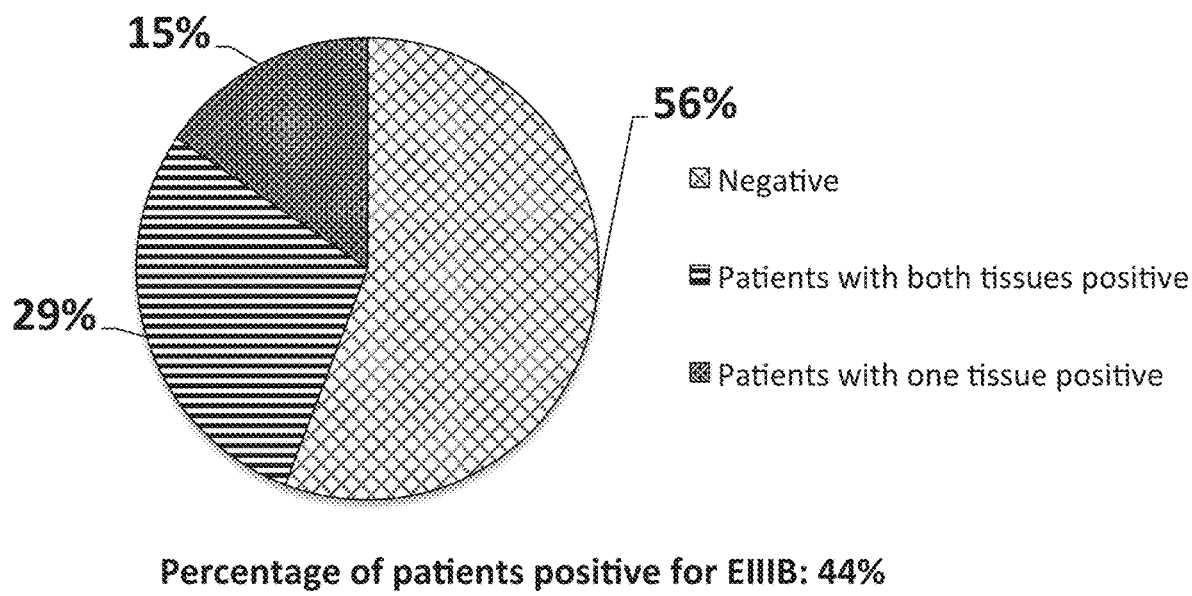

FIG. 10 shows results from immunohistochemistry with biotinylated NJB2 on a metastatic tissue array with biopsy samples from 104 patients (2 biopsies/patient) derived from multiple organs. Figure shows that 44% of the patients had metastases that were positive for stromal FN-EIIIB. This includes patients in which both biopsies were positive (29%) and those where a single biopsy was positive (15%). This is an underestimate of the number of positive metastases because tumor heterogeneity is not fully captured in the small biopsies. Table 4 lists the primary tumor sources and sites of metastases scored.

Figure 11A:
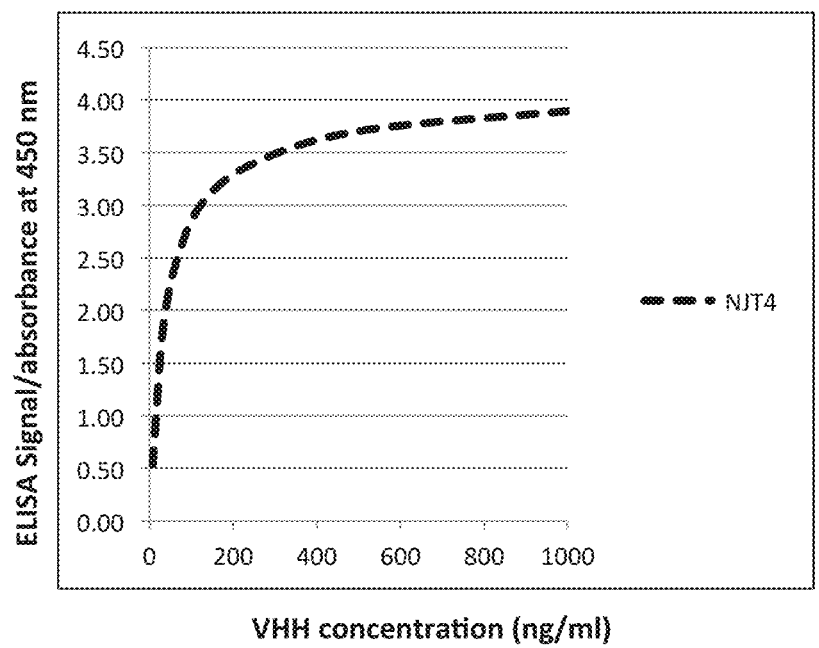
Figure 11B:
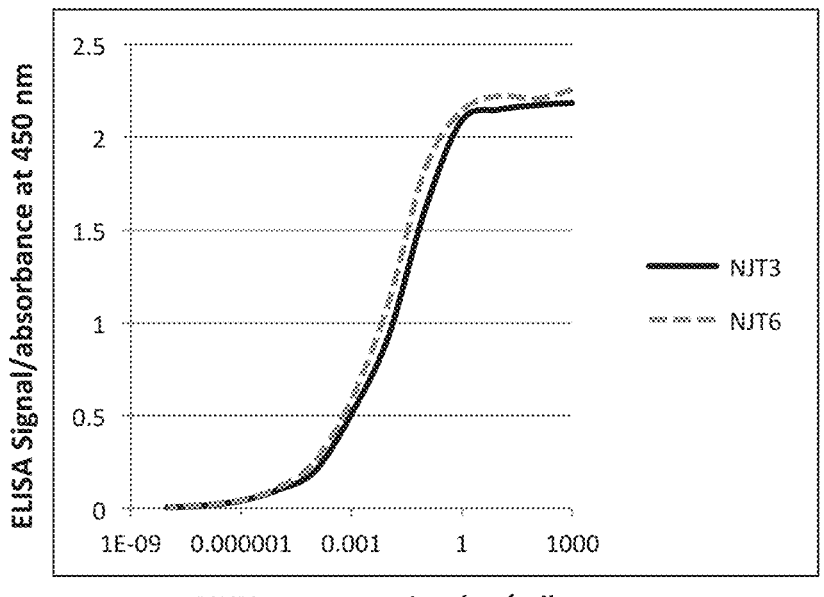

FIGS. 11A-11B show the results of ELISA assays with αTNC nanobodies NJT3, NJT4 and NJT6. ELISA plates were coated with 3 ug/ml of purified human TNC protein and increasing concentrations of the VHH NJT4 (FIG. 6A) and NJT3 and NJT6 (FIG. 6B) were tested for binding to TNC and determining binding affinities.

Figure 12:
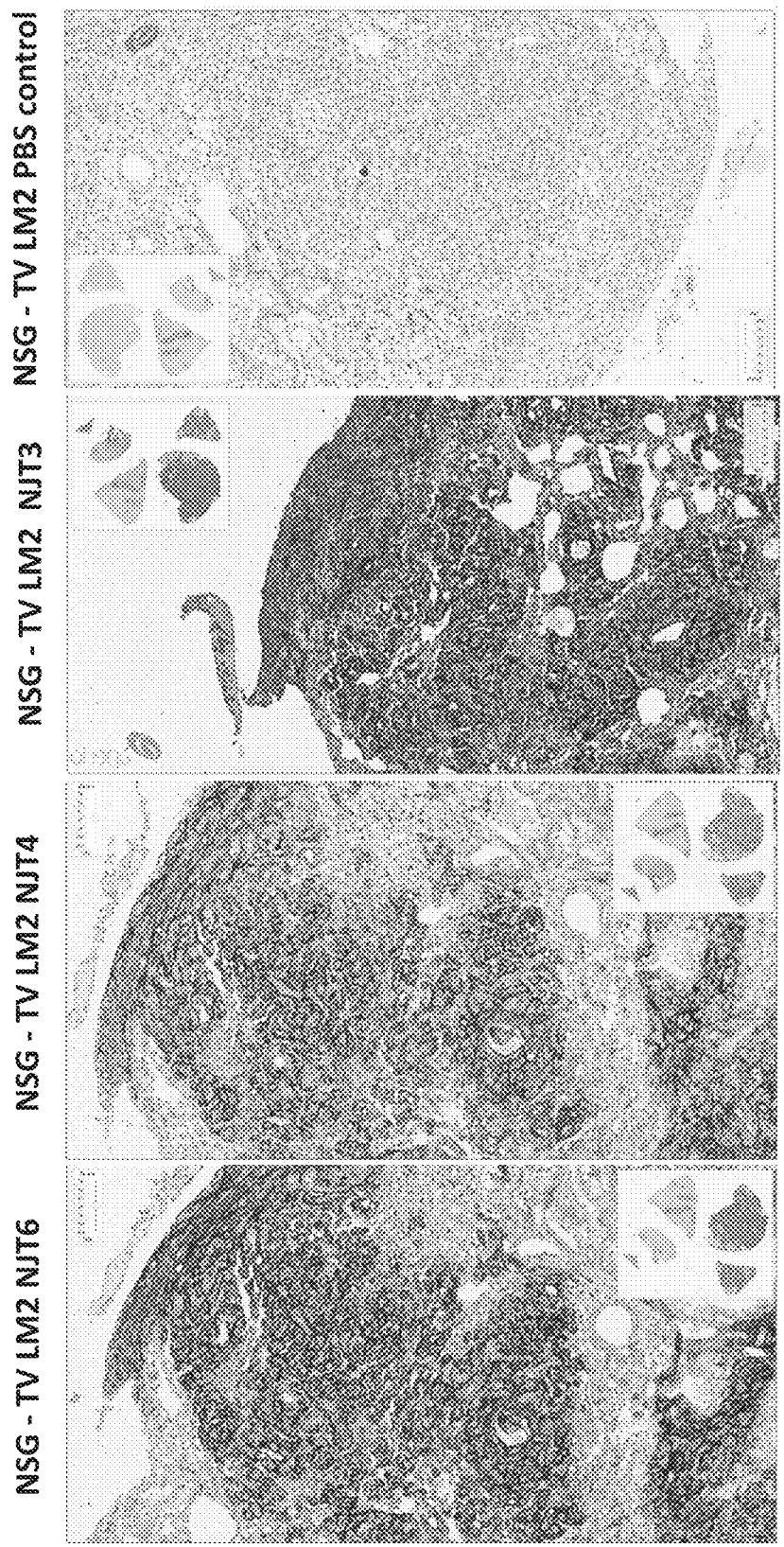

FIG. 12 shows that αTNC nanobodies NJT3, NJT4 and NJT6 specifically bind to tumor ECM. Immunohistochemistry of lung metastases of LM2-ZsGreen-Luciferase cells developed in NSG mice revealed that the nanobodies specifically recognize TNC in the metastatic ECM.

FIG. 13 shows three different anti-TNC VHHs specifically recognize tumor ECM. VHHs were site-specifically labelled with Texas Red via sortase-mediated tagging and injected into mice bearing tumors. The images were acquired using ex vivo two-photon microscopy and show an overlay of the green and red channels; tumor cells (green in the originals) are surrounded by Texas-Red labelled ECM fibrls (arrows). Images of an orthotopic LM2-Zs-Green-Luciferase tumor derived from NSG mice injected with 20 ug of the indicated Texas red-labelled VHH 120 minutes prior to imaging.

Figure 14A:
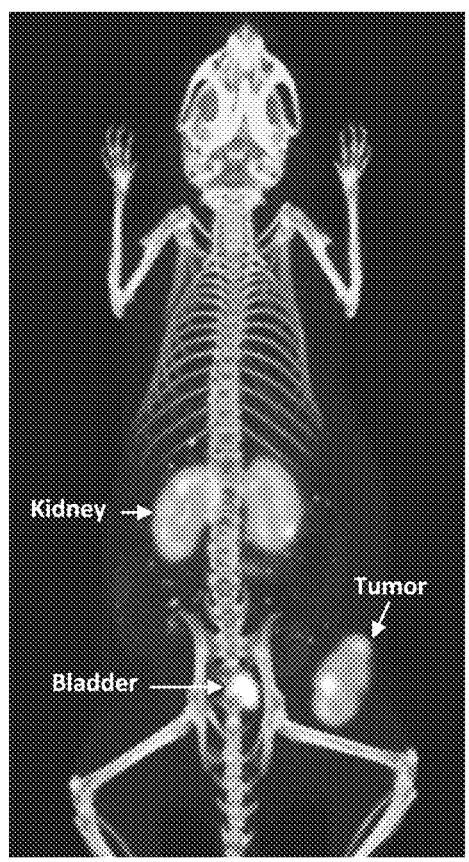
Figure 14B:
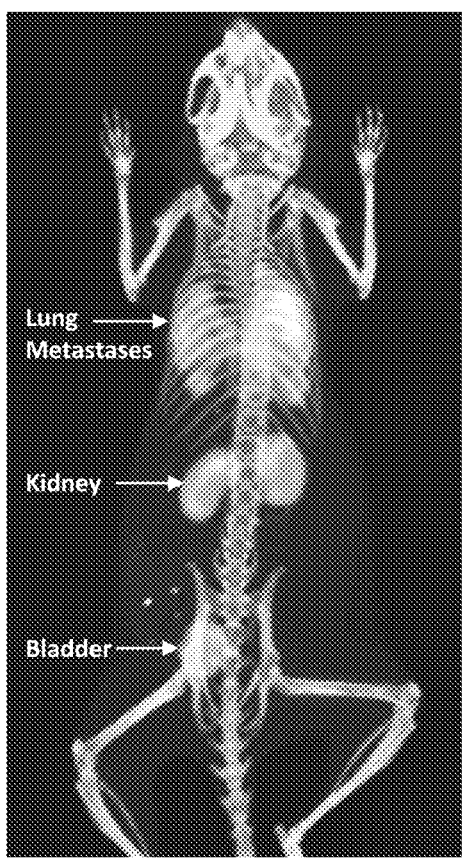

FIGS. 14A-14B show $^{64}$Cu-NJT6 anti-tenascin nanbody detects orthotopic primary tumors and lung metastases derived from LM2 TNBC human cell line: VHH-NJT6 was labelled with $^{64}$Cu using sortagging. Mice were imaged 2 h post injection of $^{64}$Cu-NJT6 (A) PET-CT images of NSG mice injected orthotopically (mammary fat pad) with LM2-ZsGreen-Luciferase TNBC cells. Labels detected in kidney, bladder and primary tumor in the left lower mammary fat pad (B) NSG mice injected via the tail vein (pulmonary metastasis model) with LM2-ZsGreen-Luciferase TNBC. Signals detected in kidney, bladder and lungs (metastases marked by arrow).

Figure 15A:
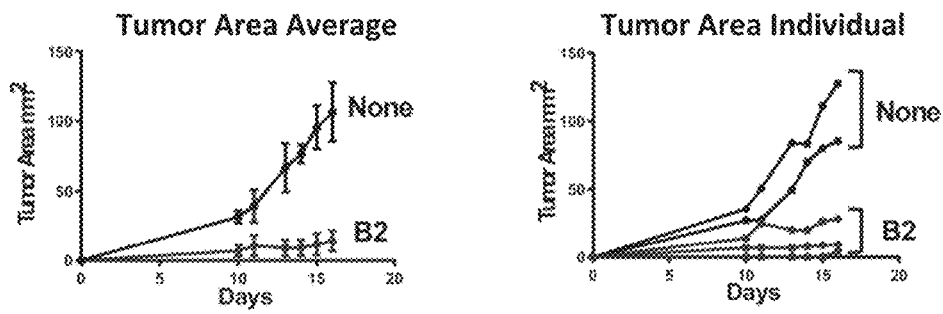
Figure 15B:
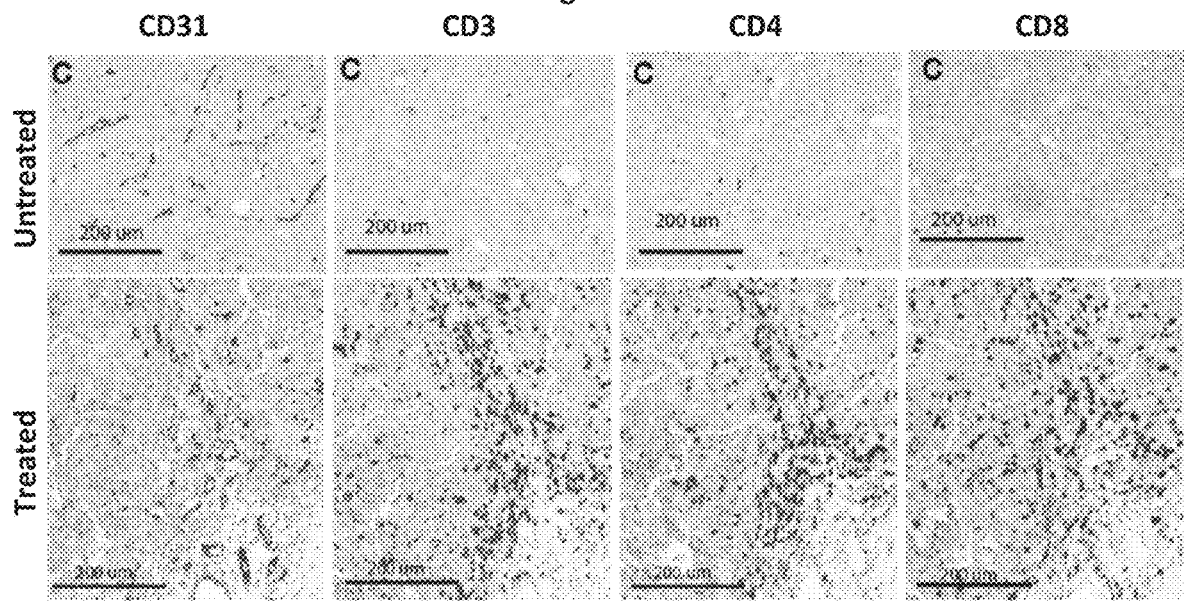
Figure 15C:
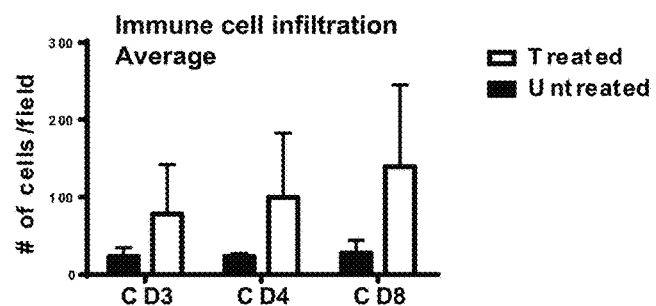

FIG. 15A shows the tumor size after B16F10 cells were implanted subcutaneously in C57BL/6 immunocompetent mice and either left untreated (None) or treated on days 4 and 11 with CAR-T cells, recognizing the EIIIB domain of fibronectin (B2). Tumors treated with anti-EIIIB-FN CAR-T cells showed markedly diminished growth rates. Parallel experiments conducted in immunodeficient RAG2 knockout mice showed very little suppression of tumor growth, indicating that host immune cells contribute to the suppression. FIG. 15B Immunohostochemistry of untreated tumor (C) or CAR-T treated tumors showing vasculature (CD31) and markedly enhanced recruitment of T cells to the treated tumor; total T cells (CD3) and CD4+ and CD8+ T cells. FIG. 15C Quantification of T cell infiltration shows greatly enhanced T cell numbers in CAR-T cell-treated tumors.

DETAILED DESCRIPTION

The extracellular matrix (ECM), including extracellular molecules secreted by cells, provides the structural and biochemical support for surrounding cells. It serves a variety of additional purposes, including segregating tissues from one another, regulating intercellular communication, providing biomechanical and biochemical support for cells and sequestering growth factors, in addition to being involved in physiological processes, such as wound healing, angiogenesis and growth. The ECM is also involved in pathophysiological processes, including tumor invasion and metastasis and other diseases associated with ECM remodeling. The composition, stiffness and elasticity of the ECM have been shown to lead to impact on gene expression, cell survival, proliferation and differentiation, and cancer progression.

Cancer is a complex disease, progressing from initiation of a primary tumor, typically via one or more mutational events leading to excessive growth of a primary tumor. So long as the primary tumor remains restricted to its site of origin, it is often possible to resect it surgically and it is often referred to as a benign tumor. However, further changes, both intrinsic to the tumor cells themselves and by recruitment of non-tumor cells that interact with the tumor cells (often called "stromal" cells), lead to progression in the state of the tumor eventually resulting in invasion into underlying tissues. Such tumors are referred to as invasive or malignant and are much harder to treat by surgery because it is difficult to ensure removal of all the tumor cells since they have invaded and spread. This problem is exacerbated by the process of metastasis, in which tumor cells detach from the primary tumor and migrate away from it, eventually penetrating into the vasculature and/or the lymphatics and spreading extensively through the body, seeding secondary tumors or metastases at distant sites. Although some metastases can be removed surgically, they are frequently numerous, may be small and hard to detect and are therefore impossible to remove by surgery. Treatment then calls for radiotherapy or chemotherapy and, despite decades of effort, these methods remain ineffective and metastatic cancer is responsible for 90% of cancer deaths. Therefore, there is a pressing need for better understanding of the mechanisms of metastasis and the development of methods to detect and eradicate metastases.

The invention described herein, in some aspects includes methods of developing nanobodies specific for proteins present in the extracellular matrix (ECM) of diseased tissues such as tumors, fibrotic tissue and atheromas, among others. These proteins are expressed in tumors, metastatic sites, fibrosis, atheromas, inflammatory disorders, aneurysms and other diseases characterized by ECM remodeling and, importantly, are nearly absent from normal adult human tissues. For example, nanobodies highly specific to an epitope in the EIIIB domain of fibronectin (FN) and to tenascin C (TNC), which are present in the ECM of diseased tissues but not in normal, healthy adult tissues, were developed. Therefore, the nanobodies generated may be used for in vivo and in vitro diagnostic imaging (such as, but not limited to, IF, IHC, PET/CT) and for diverse targeted therapeutics across a broad spectrum of diseases.

An extracellular matrix (ECM) protein, as used herein, refers to any protein recognized as being a part of the ECM. ECM is a fundamental and important component of metazoan organisms providing architectural support and anchorage for the cells. The ECM consists of a complex meshwork of highly cross-linked proteins and exists as interstitial forms within organs and as specialized forms, such as basement membranes underlying epithelia, vascular endothelium, and surrounding certain other tissues and cell types (e.g. neurons, muscles). Cells adhere to the ECM via transmembrane receptors, among which integrins are the most prominent. These cell-matrix interactions result in the stimulation of various signaling pathways controlling proliferation and survival, differentiation, migration, etc. The composition of the ECM and the repertoire of ECM receptors determine the responses of the cells. The biophysical properties of the ECM (deformability or stiffness) have also been shown to modulate these cellular functions. In addition to core ECM components (fibronectins, collagens, laminins, proteoglycans, etc.), the ECM serves as a reservoir for growth factors and cytokines and of ECM-remodeling enzymes that collaborate with ECM proteins to signal to the cells.

In particular, ECM proteins characterized by their enhanced presence in disease states such as cancer and metastasis, for example, fibronectin's (FN) EIIIA and/or EIIIB domains and tenascin C (TNC), may be used as targets for the binding of nanobodies. The EIIIA and EIIIB domains of FN and TNC have been found to be expressed in diseased states, such as in tumors, metastatic sites, fibrosis, atheromas, inflammatory disorders, aneurysms, and other diseases, while being nearly absent in healthy (non-diseased) adult tissues. Therefore, the development of nanobodies, to these selected domains can be useful to both identify the diseased tissue (and diseased state of the subject) as well as to deliver therapeutics or other cargo to the region. Other ECM proteins, or epitopes thereof, have also been shown to be selectively expressed in tumors and or metastases and could, similarly, be detected using specific nanobodies.

As shown in the Examples below, nanobody libraries against ECM proteins were generated and screened, resulting in the discovery of novel and specific nanobodies against disease-specific ECM epitopes (e.g., NJB2, NJT3, NJT4, and NJT6). In particular, as examples, the NJB2 nanobody is specific for an epitope in the EIIIB domain of fibronectin and the NJT3, NJT4, and NJT6 nanobodies are specific to human tenascin C protein. Other tumor and/or metastatic ECM proteins and domains (collectively referred to here as ECM epitopes) selectively expressed in tumors or metastases have also been described using the same proteomic methods, and they may be detected and monitored using any of the methods described herein.

The methods used according to the invention exploit very recent advances in technology combining selective enrichment of the ECM, bioinformatic definition of the complete inventory of ECM proteins encoded in the genome, and application of mass spectrometry. These methods have made possible the determination of the ECM complement of any tissue from small samples of tissue. This approach has confirmed that certain ECM proteins and domains (ECM epitopes) are present in diseased tissue at higher concentrations than in healthy tissue.

Described herein are methods for recovering nanobodies that specifically bind to ECM epitopes selectively present in diseased tissue. Several methods based on application and exploitation of these nanobodies are described herein. Methods for determining the presence of these ECM epitopes from patient samples and thus providing evidence as to whether the subjects have a particular disease and/or the disease's progression or regression are also provided. A subject's status can be determined using the specific nanobodies coupled to an active agent using standard immunological methods including immunohistochemistry, immunofluorescence, ELISA, Western blots, protein arrays, noninvasive imaging methods such as Immuno-PET/CT, and similar methods. Use of such methods provides diagnostic, prognostic and monitoring information, allowing for the improved management of patients' care and therapy.

Methods for targeting active agents such as imaging agents (e.g., radionuclides, fluorescent reporters or other detectable reagents for use in PET imaging or other imaging modalities, etc.) specifically to individual ECM epitopes within the diseased-state extracellular matrix to detect the location, extent and progression of a disease, e.g., primary tumors and/or metastases are also encompassed within the invention.

Methods for targeting active agents such as therapeutic agents (e.g., radionuclides, chemotherapeutic drugs, toxins, cytokines, siRNAs, shRNAs, nanoparticles, CAR-T cells etc.) specifically to individual ECM epitopes in order to concentrate such therapeutic agents to diseased tissue, e.g., primary tumors and/or metastases, and thus improve therapeutic index are also aspects of the invention. Targeting of the therapeutic agents may be achieved by attaching them to specific nanobodies against ECM epitopes defined in the aspects described above.

The invention also encompasses binding peptides or polypeptides, such as nanobodies, capable of interacting with ECM epitopes optionally in the form of conjugates, as described below. The binding peptides or polypeptides of the invention bind to an ECM epitope, preferably in a selective manner. An "ECM epitope" as used herein refers to a portion of the diseased state ECM which interacts with the nanobody or peptide. The epitope may comprise a domain of the ECM protein, a portion of a domain of the ECM protein, a specific posttranslational modification or may involve regions from more than one domain of the ECM protein. As used herein, the terms "selective binding" and "specific binding" are used interchangeably with respect to binding peptide or polypeptide to refer to the ability of the binding peptide or polypeptide to bind with greater affinity to a specific ECM protein and fragments thereof than to non-ECM proteins or other ECM components. That is, binding peptide or polypeptide that bind selectively to an ECM epitope will not bind to non-ECM protein or to other ECM proteins to the same extent and with the same affinity as they bind to the specific ECM epitope. In some embodiments, the binding peptide or polypeptide of the invention bind solely to the specific ECM epitopes. As used herein, a binding peptide or polypeptide that binds selectively or specifically to a specific ECM epitopes will bind with lesser affinity (if at all) to non-ECM proteins or other different ECM proteins. Lesser affinity may include at least 10% less, 20% less, 30% less, 40% less, 50% less, 60% less, 70% less, 80% less, 90% less, or 95% less.

Preferably the ECM binding peptide or polypeptide is a nanobody. The nanobodies described herein are selective for ECM epitopes that are expressed specifically in diseased tissues, such as cancer, and are largely absent or present in nominal concentrations in normal adult human tissue. Nanobodies have a number of important properties that make them advantageous compared to other antibody platforms for in vivo diagnostic imaging and targeted delivery. Compared to antibodies, nanobodies are smaller (approximately 15 kDa), which allows for a much faster clearance rate, as the renal cut-off for glomerular filtration is 60 kDa (De Vos et al., Expert Opin Biol Ther. 13(8): 1149-60 (2013)). Nanobodies also have better tissue penetration and a shorter circulatory half-life, as compared to full-sized antibodies. Furthermore, nanobodies are in vivo affinity-matured, unlike scFvs or man-made scaffolds, which allows for the isolation of highly functional (i.e. high affinity) binders. Nanobodies are also more suitable than scFvs for interacting with grooves on the surface of antigens, such as the catalytic sites of enzymes (Hassanzadeh-Ghassabeh et al., Nanomed. 8(6): 1013-26 (2013)). Camelid single-domain antibodies (VHH) share a high degree of sequence identity with human VHs and have not been found to trigger immunogenic responses in mice. Likewise, no adverse immunogenic responses in humans have been reported in current clinical trials. The nanobodies can be humanized (Rashidian et al., PNAS, 112(19): 6146-6151 (2015)), are a renewable resource, and are generally stable following the addition of active agents, such as imaging probes. Stable conjugated nanobodies can be generated and purified rapidly and reproducibly.

In some embodiments the nanobodies have an amino acid sequence that corresponds to the amino acid sequence of a naturally occurring VHH domain, but that has been "humanized," i.e., by replacing one or more amino acid residues in the amino acid sequence of the naturally occurring VHH sequence (and, in particular, in the framework sequences) by one or more of the amino acid residues that occur at the corresponding position(s) in a VH domain from a conventional four-chain antibody from a human being. Methods for humanization are well known. Humanized nanobodies may have several advantages, such as a reduced immunogenicity, compared to a corresponding naturally occurring VHH domain. "Humanization" can be performed by providing a nucleotide sequence that encodes a naturally occurring VHH domain, and then changing one or more codons in the nucleotide sequence in such a way that the new nucleotide sequence encodes a "humanized" nanobody. This nucleic acid can then be expressed to provide the nanobody. Alternatively, based on the amino acid sequence of a naturally occurring VHH domain the amino acid sequence of the humanized nanobody, can be designed and then synthesized de novo using techniques for peptide synthesis. The skilled artisan may also combine one or more parts of one or more naturally occurring VHH sequences (such as one or more FR sequences or CDR sequences), and/or one or more synthetic or semi-synthetic sequences, in a suitable manner, so as to provide a nanobody or a nucleotide sequence or nucleic acid encoding the same.

In some embodiments the term nanobody refers to analogs, mutants, variants, alleles, homologs and orthologs of the nanobodies described herein. Generally, in such analogs, one or more amino acid residues may have been replaced, deleted and/or added, compared to the nanobodies disclosed herein. Such substitutions, insertions, deletions or additions may be made in one or more of the framework regions and/or in one or more of the CDRs and, in particular, analogs of the CDRs of the nanobodies of the sequences disclosed herein including SEQ ID NOS:1-4. Exemplary CDRs are presented in Table 3.

In some embodiments, the nanobodies comprise an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with any of the amino acid sequences provided herein. In some embodiments, the amino acid sequence of the nanobody comprises an amino acid sequence provided herein.

Alternatively, a nanobody described herein may comprise up to 5 (e.g., 4, 3, 2, or 1) amino acid residue variations in one or more of the CDR regions of one of the antibodies exemplified herein and binds the same epitope of antigen with substantially similar affinity (e.g., having a KD value in the same order). In one example, the amino acid residue variations are conservative amino acid residue substitutions. As used herein, a "conservative amino acid substitution" refers to an amino acid substitution that does not alter the relative charge or size characteristics of the protein in which the amino acid substitution is made.

"Analogs," as used herein, are sequences wherein each or any framework region and each or any complementarity-determining region shows at least 80% identity, preferably at least 85% identity, more preferably 90% identity, even more preferably, 95% identity with the corresponding region in the reference sequence (i.e., FR1_analog versus FR1_reference, CDR1_analog versus CDR1_reference, FR2_analog versus FR2_reference, CDR2_analog versus CDR2_reference, FR3_analog versus FR3_reference, CDR3_analog versus CDR3_reference, FR4_analog versus FR4_reference), as measured in a BLASTp alignment.

A substitution may, for example, be a conservative substitution and/or an amino acid residue may be replaced by another amino acid residue that naturally occurs at the same position in another VHH domain. Deletions and/or substitutions may be designed in such a way that one or more sites for post-translational modification (such as one or more glycosylation sites) are removed or to introduce one or more sites for attachment of functional groups, for example, to allow site-specific pegylation.

The amino acid residues of the nanobody can be modified, i.e., on the protein backbone or on a side chain). Modifications include the introduction of one or more functional groups, residues or moieties into or onto the nanobody. The functional groups may be linked directly to a nanobody or indirectly through a linker or spacer. Methods for increasing the half-life and/or reducing immunogenicity of pharmaceutical proteins involve attaching a polymer, such as poly (ethyleneglycol) (PEG) or derivatives thereof (such as methoxypoly(ethyleneglycol) or mPEG). For example, PEG may be attached to a cysteine residue that naturally occurs in a nanobody or is synthetically added to a nanobody at the terminus or within the nanobody. In some embodiments PEG has a molecular weight of more than 5000 and less than 100,000 or more than 10,000 and less than 200,000. Other modifications include N-linked or O-linked glycosylation, usually as part of co-translational and/or post-translational modification, depending on the host cell used for expressing the nanobody. The nanobodies may be obtained from selecting from libraries of such VHH domains, e.g., a phage library. A phage library can be created by inserting a library of polynucleotides containing antibody VHH domains from the B-cells of an immunized animal. The diversity of a phagemid library can be manipulated to increase and/or alter the specificities of the polypeptides of the library to produce and subsequently identify additional, desirable, molecular properties and the polynucleotides encoding them. Libraries involve high levels of diversity because it is possible to introduce 1 of 32 different codons in every position and all 20 amino acids. Such a library theoretically grows by $32^n$ for every n number of residues. Synthesis of oligonucleotides with selected nucleotide "degeneracy" at certain positions is known in that art. Phage display libraries typically have $10^9$ to $10^{10}$ "entries."

Methods of making nanobody libraries generally involve immunization of a camelid (e.g., camel, dromedary, alpaca, vicuna, llama, etc.) with the material to be immunized against i.e., a preparation of the diseased tissue. For example, as described in the Examples section, an alpaca may be immunized with a specific ECM preparation from a human cancer patient to generate alpaca-derived nanobodies specific for ECM protein epitopes associated with the disease. Lymphocytes can then be isolated from blood samples, and lymphocyte RNA can then be used to construct phage display-based nanobody libraries, for example using an M13 phage. The libraries can then be screened for novel nanobodies against a diverse set of ECM and ECM-associated antigens involved in disease. The methods involve harvesting peripheral blood lymphocytes from which nucleic acid can be isolated. The nucleic acid from which the VH domain sequences derive may be total RNA or, more specifically mRNA isolated from the cells within the sample taken from the host. The expression vectors may be any suitable vectors used for library construction, and are preferably phage or phagemid vectors allowing selection of target-specific antibody fragments using phage-display-based selection methods. The antibody sequences isolated from these libraries may then be used as scaffolds for in vitro affinity maturation to further improve binding to the target antigen. The immunogen used is directly derived from the diseased ECM of human cancer metastases samples, or is a set of ECM proteins present at disease site, individually mixed to prepare a cocktail for immunization. The libraries contain sequences of VHHs that bind diverse components of this diseased ECM. The nanobodies can readily be site-specifically tagged at their N- or C-terminus with different active agents, facilitating their use in imaging and/or therapeutic applications.

The invention encompasses methods of generating nanobodies against ECM epitopes in a high-throughput manner. As a non-limiting example, a method is provided of generating ECM protein binders such as nanobodies, specifically binding to an epitope of ECM proteins associated with a disease state, and preferably isolated from a diseased tissue, by (i) immunizing an animal with an ECM protein sample from a diseased tissue and (ii) screening for nanobodies specifically binding to an epitope of an ECM protein from a diseased tissue.

In some embodiments, the nanobodies or other peptides described herein specifically bind to the corresponding target epitope. A nanobody or peptide such as an antibody that "specifically binds" to an epitope is a term well understood in the art. A molecule is said to exhibit "specific binding" if it reacts more frequently, more rapidly, with greater duration and/or with greater affinity with a particular target antigen than it does with alternative targets. A nanobody "specifically binds" to a target antigen or epitope if it binds with greater affinity, avidity, more readily, and/or with greater duration than it binds to other substances.

For example, a nanobody that specifically (or preferentially) binds to an antigen or an antigenic epitope therein is a nanobody that binds this target antigen with greater affinity, avidity, more readily, and/or with greater duration than it binds to other antigens or other epitopes in the same antigen. It is also understood with this definition that, for example, a nanobody that specifically binds to a first target antigen may or may not specifically or preferentially bind to a second target antigen. As such, "specific binding" or "preferential binding" does not necessarily require (although it can include) exclusive binding. In some examples, a nanobody that "specifically binds" to a target antigen or an epitope thereof may not bind to other antigens or other epitopes in the same antigen.

In some embodiments, a nanobody as described herein has a suitable binding affinity for the target antigen or antigenic epitopes thereof. As used herein, "binding affinity" refers to the apparent association constant or $K_A$. The $K_A$ is the reciprocal of the dissociation constant ($K_D$). The nanobody described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of a nanobody for a first antigen relative to a second antigen can be indicated by a higher $K_A$ (or a smaller numerical value $K_D$) for binding the first antigen than the $K_A$ (or numerical value $K_D$) for binding the second antigen. In such cases, the nanobody has specificity for the first antigen (e.g., a first protein in a first conformation or mimic thereof) relative to the second antigen (e.g., the same first protein in a second conformation or mimic thereof; or a second protein).

For example, in some embodiments, the anti-ECM nanobodies described herein have a higher binding affinity (a higher $K_A$ or smaller $K_D$) to a first ECM epitope as compared to the binding affinity to a second ECM epitope. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[Bound]=[Free]/(Kd+[Free])$$

It is not always necessary to make an exact determination of $K_A$ or $K_D$ though, since sometimes it is sufficient to obtain a quantitative measurement of affinity, e.g., determined using a method such as ELISA or FACS analysis, is proportional to $K_A$ or $K_D$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

Further steps may include, for example and without limitation, a step of affinity maturation, a step of expressing and/or modifying the desired amino acid sequence, a step of screening for binding and/or for activity against the desired antigen (ECM epitope), a step of determining the desired amino acid sequence or nucleotide sequence, a step of introducing one or more humanizing substitutions, a step of formatting in a suitable multivalent and/or multispecific format, a step of screening for specific desired biological and/or physiological properties.

ECM remodeling is typical of a number of diseases and at least some of the ECM biomarker epitopes are shared among these diseases. The nanobodies bio-panned as described in the Examples below can therefore be applicable to a wide range of diseases characterized by ECM remodeling.

The binding reagents useful according to the invention in some embodiments are isolated VHH antibody fragments, so-called nanobodies. "Isolated nanobodies" as used herein refer to polypeptides that are substantially physically separated from other cellular material (e.g., separated from cells which produce the nanobodies) or from other material that hinders their use either in the diagnostic or therapeutic methods of the invention. In particular, the peptides are sufficiently pure and are sufficiently free from other biological constituents of their host cells so as to be useful in, for example, producing pharmaceutical preparations or sequencing. Because isolated nanobodies of the invention may be admixed with a pharmaceutically acceptable carrier in a pharmaceutical preparation, they may comprise only a small percentage by weight of the preparation. The nanobody is nonetheless substantially pure in that it has been substantially separated from the substances with which it may be associated in living systems.

In some embodiments the CDRs or other portions of the nanobodies disclosed herein are incorporated into a structure other than a nanobody. For instance a humanized antibody comprising one or more of the CDRs of the nanobodies disclosed herein or analogs thereof may be produced and used according to the invention. Thus, the peptide may be an antibody.

In other embodiments, the peptides of nanobodies described herein may be conjugated to other molecules, for instance, to enhance delivery. The peptides or nanobodies may be conjugated in some embodiments to an antibody.

The term "antibody" herein is used in the broadest sense and specifically covers intact monoclonal antibodies, multispecific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

An active agent, such as imaging probes (fluorophores, PET tracers, radio-isotopes, etc.), cytokines, ECM remodeling enzymes, toxins, siRNAs, shRNAs, nanoparticles, CAR-T cells, drugs, or other forms, can be very readily site-specifically attached to the nanobodies for targeted delivery to diseased sites. For example, the nanobodies may be site-specifically tagged at their N- or C-terminus via sortase-mediated reactions ("sortagging")(Guimaraes et al-Site-specific C-terminal and internal loop labeling of proteins using sortase-mediated reactions.). This attachment greatly facilitates targeted delivery of any cargo attached to the nanobodies to diseased ECM epitopes.

This targeted approach offers numerous advantages over traditional systemic therapies because it permits selective accumulation in tumor and disease ECM, resulting in increased specificity and sensitivity of detection and/or treatment and the reduction of background and off-target toxicity. Furthermore, while other targeted therapies are often challenged by systemic toxicities due to wider expression of the targeted proteins (Hansel et al., Nat Rev Drug Discov, 9(4): 325-338 (2010)); the selective expression of FN's EIIIB domain and TNC in diseased sites (or of other tumor-specific ECM epitopes) and specific binding of nanobodies to their respective target proteins avoids the systemic toxicities faced by other targeted therapies. The nanobodies are also small in size (approximately 15 kDa) and are therefore rapidly cleared from the subject, resulting in reduced systemic effects.

Unlike other targeted therapies, for example, HER2-specific nanobodies for breast and ovarian cancer and Rituximab for lymphoid tumors, the nanobodies described herein can be broadly therapeutic/targeting agents, as they recognize antigens associated with diseased ECM, not solely confined to specific cancer types. Additionally, some of the nanobodies disclosed herein can recognize target antigens expressed in other disease states characterized by ECM remodeling. Such disease states include, but are not limited to, cardiovascular disorders, such as atheroma, aneurysms, and myocardial infarction, fibroses, and inflammatory disorders. Compared to tumor-cell targeting therapies, such as anti-CD30 and anti-CD20, which may have limited efficacy due to tumor cell heterogeneity and the genomic instability of tumor cells, the nanobodies described herein target specific ECM protein epitopes, which are less heterogeneous and more stable. Tumor-cell targeting therapies also lack efficacy due to decreased or heterogeneous target expression, receptor internalization, and drug efflux. In contrast, ECM proteins rarely have mutations in cancer and the ECM is abundant and accessible. In the particular examples presented, fibronectin and tenascin C are major constituents of tumor ECM. Using the proteomic data described herein and elsewhere, additional tumor and/or metastasis-specific ECM proteins and related nanobodies can be similarly isolated and identified from the M13 phage libraries.

Local administration therapies suffer from a different shortcoming: they are not efficient at treating metastases, which are typically multiple and widely distributed. However, systemic administration of nanobodies allows them to access all diseased tissue, including both primary tumors and metastatic sites, throughout the body and bind selectively to tumor and/or diseased ECM.

As used herein, an isolated tissue sample is tissue obtained from a tissue biopsy, a surgically resected tumor, or any other tumor mass removed from the body using methods well known to those of ordinary skill in the related medical arts. The tissue may be known to be diseased or suspected of being diseased, for example, the tissue may be known to be cancerous or suspected of being cancerous. The phrase "suspected of being cancerous" as used herein means a cancer tissue sample believed by one of ordinary skill in the medical arts to contain cancerous cells. Methods for obtaining the sample from a biopsy include gross apportioning of a mass, microdissection, laser-based microdissection, or other art-known cell-separation methods. The tissue may also be a histological section.

Because of the variability of the cell types in diseased-tissue biopsy material, and the variability in sensitivity of the predictive methods used, the sample size required for analysis may be 5 mg, 10 mg, 15 mg, 25 mg, 30 mg, or 50 mg or greater of tissue. Alternatively, it may be portions or sections of biopsy-sized tissue samples. The appropriate sample size may be determined based on the cellular composition and condition of the biopsy and the standard preparative steps for this determination and subsequent isolation of the proteins for use in the invention are well known to one of ordinary skill in the art.

Alternatively, the ECM proteins may be analyzed directly in a body. For instance, one or more binding peptide or polypeptides such as nanobodies, capable of recognizing one or more of the diseased ECM protein epitopes may be administered to the subject directly. The binding peptide or polypeptides may be labeled, for example with fluorescent, NIR, luminescent or PET probes in order to assist with visualization of the ECM. Alternatively, other binding peptide or polypeptides may be used to provide visualization of the ECM. In other embodiments the tissues may be removed from the subject before exposure to the binding peptide or polypeptides.

The invention may be used to examine changes in the diseased state of a subject. A diseased state is any physiological condition in a subject caused by under- or overproduction of a biochemical in the subject, invasion of the subject by a foreign organism, i.e., an organism that produces substances that are toxic to the host, or abnormal proliferation of a part of the subject. For example, a diseased state includes, conditions associated with infections, cancers, metastasis, etc. and many of these disease states are associated with excessive production and alteration of ECM, which can be targeted by the nanobodies of this invention. Changes in the metastatic state of tumors can be examined over time and/or in response to therapeutic interventions. In order to achieve these methods, tissue samples may be isolated from a subject at different times and/or with or without drug treatments. The different tissue samples can be analyzed for the presence of the diseased-state ECM epitopes. Then the differences in ECM epitope expression between the two or more samples can be assessed. The differences can be analyzed qualitatively (e.g. by immunohistochemistry, IHC) through assessment of the different proteins present or quantitatively by measuring levels or approximate levels of protein expression (e.g., by ELISA). Alternatively, the methods of the invention may also be performed in vivo without removal of a tissue sample.

The methods of the invention involve the derivation, validation and deployment of nanobodies highly specific for ECM epitopes specifically expressed in cancer, metastasis and other disease states. These unique, highly effective antibodies may be used as conjugated nanobodies in order to enable highly selective means of delivery (with low systemic background) of imaging probes (fluorescent, radioactive, PET etc) and other agents including but not limited to pharmaceuticals, toxins, antibodies, immune modulators, siRNAs, shRNAs, nanoparticles, CAR-T cells to an accessible, prevalent, stable extracellular component of diseased tissue. Conjugation techniques, imaging agents, active agents, methods of preparing and imaging these unique antibodies are known in the art, and a brief summary of these is included herein.

The presence of a protein in a tissue sample or the level of a protein in a tissue sample may be assessed using any known methods in the art. Such methodologies are well known. A method commonly used in clinical and pathological assessment is immunohistochemistry or immunofluorescence, which allows determination of the presence of particular proteins or sets of proteins in a tissue sample. The methods of immunohistochemistry and immunofluorescence are well known and widely practiced. When a quantitative assessment of protein levels is made, the levels of protein may be compared with either a reference or threshold amount or with amounts found in other samples. For instance, if the presence or levels of proteins are measured in a primary tumor and its metastasis or a corresponding normal tissue, those can be compared to provide a relative assessment of the progression of the tumor or its metastases. Alternatively, the levels may be compared with an amount that is known (or is shown) to be an amount above or below which a tumor normally expresses the protein. The value that is used in the comparison is referred to as the reference or threshold level.

The actual numbers in the particular determination of threshold values may vary for different tumors or under different circumstances, such as the conditions of the assay to determine expression. However, the skilled artisan would be able to identify the correct threshold values based on the circumstances. For example, threshold values could easily be generated using normal non-cancerous tissue under similar circumstances.

The reference sample can be any of a variety of biological samples against which a diagnostic assessment may be made. Examples of reference samples include biological samples from control populations or control samples. Reference samples may be generated through manufacture to be supplied for testing in parallel with the test samples, e.g., reference sample may be supplied in diagnostic kits. Appropriate reference samples will be apparent to the skilled artisan.

In other embodiments, the expression level of the protein in the test sample may be determined based on a direct comparison to a reference level in absolute values. For instance, at least 10%, at least 20%, at least 50%, at least 100%, at least 200%, at least 500%, at least 1000% or more higher than the expression level of the protein in the reference sample. In other embodiments, the expression level of the protein in the test sample is at least 10%, at least 20%, at least 50%, at least 100%, at least 200%, at least 500%, at least 1000% or more lower than the expression level of the protein in the reference sample.

In further embodiments, the expression levels of one or more ECM epitopes in a subject are determined at a first time point and at a later second time point. Expression levels of the one or more ECM epitopes may additionally be measured at further subsequent times, so that the total number of measurements may be 3, 4, 5, 6, 7, 8, 9, 10, or more. The separation in time between any two measurements may be a matter of days, or it may be longer, e.g., weeks, months, or years. For example, the time between obtaining samples is 6 months, 8 months, 10 months, 1 year, 1.5 years, 2 years, 2.5 years, 3 years, 3.5 years, 4 years, 4.5 years, or 5 years. The time between obtaining a first (or earlier) sample and obtaining a subsequent or successive sample the subject may be a time sufficient for a change disease status to occur. The progression or regression of a disease may be determined by comparing the ECM epitope expression levels in isolated tissue samples between two or more time points. For example, changes in the presence or absence of the one or more ECM epitopes or their expression levels between successive time points may indicate the progression of a disease, such as to an advanced stage of the disease. In particular, higher expression levels and/or the presence of the one or more ECM epitopes in a sample taken at a later time point may indicate that a disease has progressed to an advanced stage. In some instances, the disease may be cancer, and higher expression levels or wider distribution of ECM epitopes associated with a diseased state in a sample taken at a later time point may indicate that metastatic cancer has progressed. Conversely, if an isolated tissue sample from a second time point has lower expression levels of ECM epitopes associated with a diseased state compared to an isolated tissue sample from the first time point, the disease has regressed to a less advanced stage. For example, a successive lower expression level measurement could indicate that a cancer has regressed to a less metastatic state.

The diseased state may be any non-physiological state, such as cancer, atherosclerosis, myocardial infarction, fibrosis, or a wound. In some instances, the cancer is metastatic cancer.

The presence/absence or levels of proteins or markers may be determined using any of a number of techniques available to the person of ordinary skill in the art for protein analysis, e.g., direct physical measurements (e.g., mass spectrometry), or binding assays (e.g., immunohistochemistry, immunoassays, agglutination assays, and immunochromatographic assays) etc. The method may also comprise measuring a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding domains through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring protein epitope levels may use solid phase or homogenous formats. Suitable assay methods include sandwich or competitive binding assays. Examples of sandwich immunoassays are described in U.S. Pat. No. 4,168,146 to Grubb et al. and U.S. Pat. No. 4,366,241 to Tom et al., both of which are incorporated herein by reference. Examples of competitive immunoassays include those disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

Multiple ECM epitopes may be measured using a multiplexed assay format, e.g., multiplexing through the use of nanobody arrays, multiplexing using spectral discrimination of labels, multiplexing by flow cytometric analysis of binding assays carried out on particles.

Detection of a protein epitope in a test sample involves routine methods. The skilled artisan can detect the presence or absence of a protein using well known methods. Such methods include diverse immunoassays. In general, immunoassays involve the binding of antibodies or similar probes to proteins in a sample such a histological section or binding of proteins in a sample to a solid phase support such as a plastic surface. Detectable antibodies are then added which selectively bind to the protein of interest. Detection of the antibody indicates the presence of the protein. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described in Immunoassays for the 80's, A. Voller et al., Eds., University Park, 1981, which is incorporated herein by reference.

Simple immunoassays such as a dot blot and a Western blot involve the use of a solid phase support which is contacted with a test sample. Any proteins present in the test sample bind the solid phase support and can be detected by a specific, detectable antibody preparation. The intensity of the signal can be measured to obtain a quantitative readout, such as with an ELISA. Other more complex immunoassays include forward assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, in a forward sandwich assay a third detectable antibody, which binds the second antibody is added to the system. Other types of immunometric assays include simultaneous and reverse assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional assays. A reverse assay involves the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody.

A number of methods are well known for the detection and quantification of antibodies. For instance, antibodies can be detectably labeled by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

The methods of the invention include methods for in vivo imaging using nanobodies having detectable labels. For instance The in vivo imaging methods may include PET (Positron Emission Tomography) imaging. PET imaging technologies enable high quality visualization of physiological processes at the molecular level in real time. PET is therefore highly useful in clinical diagnostics and drug development. A number of technical improvements in PET technology have been developed including in the field of tracer development, both progress in labelling strategies and an intelligent design of selective molecular probes with the capability to visualize molecular targets involved in physiological and pathophysiological processes, however, early detection of some tumors and micrometastases remains a challenge. Applicants have discovered that the Immuno-PET/CT using the unique nanobodies developed according to the invention, provide unexpected improvements in the technology and significantly improve visualization of early stage cancers and small metastases compared to conventional imaging modalities of FDG-PET/CT. As shown in FIG. 4, the images generated using the nanobodies of the invention are significantly better quality than such prior methods.

A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Labels include any known labels that can be used with imaging techniques, such as PET isotopes, scintigraphy, NMR, etc. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, as well as nanoparticles, etc. The label may be bound to a reagent during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the reagents described herein, or will be able to ascertain such, using routine experimentation. Furthermore, the coupling or conjugation of these labels to the reagents of the invention can be performed using standard techniques common to those of ordinary skill in the art. Therapeutic agents can also be delivered singly and in combinations by nanoparticles of various types and these could be targeted to disease-specific ECM by conjugation with nanoparticles allowing enrichment in the disease site.

Another labeling technique which may result in greater sensitivity consists of coupling the molecules described herein to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the binding peptide or polypeptides including antibodies or fragments thereof such as the nanobodies described here to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide $^{99}$mTc; for positron-emission tomography (PET): positron-emitting isotopes, $^{18}$F-fluorodeoxyglucose ($^{18}$FDG), $^{18}$F-fluoride, copper-64, gadodiamide, and radioisotopes of Pb(II) such as 203Pb; 111In.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

Thus, the invention contemplates ECM protein binding peptide or polypeptides, such as nanobodies, which may optionally be conjugated to an active agent, such as a detectable label for use in the methods of the invention. The active agent may be conjugated to the N-terminus or the C-terminus or internal amino acids of the nanobody. In other aspects, the invention contemplates ECM protein binding peptide or polypeptide (e.g., nanobodies) directly conjugated to an active agent. An ECM protein binding peptide or polypeptide is directly conjugated to an active agent if the active agent is linked directly (e.g., via a peptide bond) to an amino acid (i.e., N-terminal amino acid, C-terminal amino acid, or internal amino acid) of the ECM protein binding peptide or polypeptide. Alternatively, the ECM protein binding peptide or polypeptidemay be indirectly conjugated to an active agent if a linker is used to connect the active agent to the ECM protein binding peptide or polypeptide or the two components may be linked indirectly to one another by linkage to a common carrier molecule.

Thus, linker molecules ("linkers") may optionally be used to link the ECM protein binding peptide or polypeptide to another molecule (e.g. in multi- or bispecific antibodies). Linkers may be peptides, which consist of one to multiple amino acids, or non-peptide molecules. Examples of peptide linker molecules useful in the invention include glycine-rich peptide linkers (see, e.g., U.S. Pat. No. 5,908,626), wherein more than half of the amino acid residues are glycine. Preferably, such glycine-rich peptide linkers consist of about 20 or fewer amino acids. A specific advantage of the nanobodies is that, during the isolation, subcloning and expression of cloned DNA sequences encoding VHH domain nanobodies, short peptide tags are incorporated that are recognized by sortase enzymes that perform facile conjugation via these tags to other entities (Guimares et al).

A carrier molecule may include, for instance, a PEG or TEG molecule. A PEG or TEG carrier-modified peptide would be referred to as a PEGylated or TEGylated peptide.

Linker molecules may also include non-peptide or partial peptide molecules. For instance the ECM protein binding peptide or polypeptide may be linked to other molecules using well known cross-linking molecules such as glutaraldehyde or EDC (Pierce, Rockford, Ill.). Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage.

Homobifunctional cross-linker molecules have two reactive sites which are chemically the same. Examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., discuccinimyidyl suberate, dithiobis(succinimidyl propionate), and soluble bis-sulfonic acid and salt thereof.

Preferably, a bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the invention include, without limitation, m-maleimidobenzoyl-N-hydroxysuccinimide ester; m-maleimido-benzoylsulfosuccinimide ester; γ-maleimidobutyric acid N-hydroxysuccinimide ester; and N-succinimidyl 3-(2-pyridyl-dithio)propionate.

The carboxyl terminal amino acid residue of the ECM protein binding peptide or polypeptides described herein may also be modified to block or reduce the reactivity of the free terminal carboxylic acid group, e.g., to prevent formation of esters, peptide bonds, and other reactions. Such blocking groups include forming an amide of the carboxylic acid group. Other carboxylic acid groups that may be present in polypeptide may also be blocked, again provided such blocking does not elicit an undesired immune reaction or significantly alter the capacity of the ECM protein binding peptide or polypeptide to specifically function.

Suitable biologically active variants of native or naturally occurring ECM protein binding peptide or polypeptide can be fragments, analogues, and derivatives of that binding peptide or polypeptide. By "analogue" is intended an analogue of either the native polypeptide or of a fragment of the native polypeptide, where the analogue comprises a native polypeptide sequence and structure having one or more amino acid substitutions, insertions, or deletions. A ECM protein nanobody or antibody fragment is a peptide that is identical to or at least 90% homologous to less than a full length ECM protein binding nanobody or antibody, referred to herein as a portion of nanobody or antibody. The portion of nanobody or antibody is representative of the full length nanobody or antibody polypeptide. A fragment is representative of the full length nanobody or antibody if it includes at least 2 amino acids (contiguous or non-contiguous) of the nanobody or antibody and binds to the ECM protein. In some embodiments the portion is less than 90% of the entire native nanobody or antibody. In other embodiments the portion is less than 50%, 45%,40%, 35%, 30%, 25%, 20%, 15%, 10%, or 5% of the entire native nanobody or antibody. By "derivative" is intended any suitable modification of the polypeptide of interest, of a fragment of the polypeptide, or of their respective analogues, such as glycosylation, phosphorylation, polymer conjugation (such as with polyethylene glycol), or other addition of foreign moieties, so long as the desired biological activity of the nanobody or antibody is retained. Methods for making polypeptide fragments, analogues, and derivatives are generally available in the art.

The active agent may be a detectable label as described above. Such compounds are useful in vitro or in vivo for detecting and characterizing tumor cells.

The binding peptide or polypeptide may be conjugated to an active agent that is a drug or therapeutic, such as an anti-cancer drug. Such compounds may be used as therapeutic conjugates to treat diseases and tumors.

The therapeutic conjugates include a binding peptide or polypeptide such as the nanobodies described herein conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i.e., a radioconjugate) or a CAR-T cell. Other antitumor agents that can be conjugated to the binding peptide or polypeptides of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877, 296). Enzymatically active toxins and fragments thereof which can be used in the conjugates include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes.

For selective destruction of the cell, the antibody may be conjugated a highly radioactive atom. A variety of radioactive isotopes are available for the production of radioconjugated antibodies. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the conjugate is used for detection, it may comprise a radioactive atom for scintigraphic studies, for example $^{99m}$Tc or $^{123}$I, or a spin label for nuclear magnetic resonance (NMR) imaging (also known as magnetic resonance imaging, mri), such as $^{123}$I, $^{131}$I, $^{111}$In, $^{19}$F, $^{13}$C, $^{15}$N, 17O, Gadolinium, Manganese or Iron.

The radio- or other labels may be incorporated in the conjugate in known ways. For example, the binding peptide or polypeptide may be biosynthesized or may be synthesized by chemical amino acid synthesis using suitable amino acid precursors involving, for example, fluorine-19 in place of hydrogen. Labels such as $^{99m}$Tc or $^{123}$I, $^{186}$Re, $^{188}$Re and $^{111}$In can be attached via a cysteine residue in the peptide. Yttrium-90 can be attached via a lysine residue. The IODO-GEN method (Fraker et al (1978) Biochem. Biophys. Res. Commun. 80: 49-57) can be used to incorporate iodine-123.

"Monoclonal Antibodies in Immunoscintigraphy" (Chatal, CRC Press 1989) describes other methods in detail.

In other aspects, the selective destruction of the cells may be mediated by CAR-T cells with a chimeric antigen receptor. A CAR-T cell, as used herein, refers to T cells into which a chimeric receptor has been introduced to redirect their specificity towards an antigen of choice. Such receptors comprise an ectodomain that recognizes antigen independent of MHC restriction, in combination with cytoplasmic signaling domains. Many different peptides can be introduced into the T cells as the ectodomain of the chimeric antigen receptors. Examples include a nanobody, a monoclonal antibody, a humanized antibody, a chimeric antibody, a human antibody, or an antibody fragment. In one embodiment, the peptide is a nanobody.

In one embodiment, the disclosure provides a cell (e.g., T cell) engineered to express a CAR wherein the CAR-T cell exhibits an antitumor property. The CAR can be engineered to comprise an ectodomain peptide fused to an intracellular signaling domain of the T cell antigen receptor complex Zeta chain (e.g., CD3 Zeta). The CAR when expressed in a T cell is able to redirect antigen recognition based on the antigen binding specificity. An exemplary antigen is a diseased state ECM epitope that is present in greater amounts in a diseased tissue than in a normal tissue. The invention includes any antigen-binding peptide, whose cognate antigen is present in greater amounts in a diseased tissue than in a normal tissue, which when bound to its cognate antigen, affects a tumor cell so that the tumor cell fails to grow, is prompted to die, or otherwise is affected so that the tumor burden in a patient is diminished or eliminated. The antigen binding peptide is preferably fused with an intracellular domain from one or more of a costimulatory molecule and a Zeta chain. In some embodiments, the antigen binding peptide is fused with one or more intracellular domains selected from the group of a CD137 (4-1BB) signaling domain, a CD28 signaling domain, a CD3 Zeta signal domain, and any combination thereof.

In some embodiments, the antigen-binding peptide is a nanobody. In some embodiments, the nanobody is a nanobody specific for and directly binding to a diseased-state ECM epitope. In one embodiment, the diseased-state ECM epitope is EIIIA or EIIIB domain of fibronectin. In another embodiment, the diseased-state ECM epitope is Tenascin C or an epitope of Tenascin.

In some aspects, the disclosure provides a method of generating a CAR-T cell by generating a chimeric antigen receptor construct. A chimeric antigen receptor construct, as used herein, refers to a vector comprising a nucleic acid encoding a desired CAR, including an ectodomain of a peptide, a hinge and transmembrane domain, and intracellular signaling domain such as those of human 4-1BB and CD3-zeta. Such a vector is capable of introducing the desired CAR into the cells. In some instance, the vector is a lentiviral vector. In some aspects, the ectodomain of the CAR is a nanobody. In other aspects, the ectodomain of the CAR is a monoclonal antibody, a humanized antibody, a chimeric antibody, a human antibody, or an antibody fragment. In some embodiments, the CAR of the invention comprises anti-EIIIB nanobody, human CD8 hinge and transmembrane domain, and intracellular signaling domains. In some embodiments, the CAR of the invention comprises a nucleic acid sequence set forth in SEQ ID NOs:1-4.

Natural killer cells (NK Cells) are peripheral blood lymphocytes that play a role in innate immune function. NK cells express a variety of activating and inhibitory receptors that are responsible for discriminating between healthy cells, and virally infected cells or cancerous cells. Unlike T cells, NK cells exert their cytotoxic effect on target cells in an antigen independent manner. As a result, NK cells do not require antigen priming and can display robust cytotoxicity in the absence of specific antigen.

CARs can introduce a certain antigen specificity to an immune effector cell, such as NK cells. Thus, the compositions of the invention include pharmaceutical compositions comprising NK cells, both primary cells and cell lines that have been engineered with at least one chimeric antigen receptor.

In a certain embodiment, the engineered NK cells comprise a plurality of cells that are greater than 25% positive for an ECM protein bound by a nanobody as described herein. In a certain embodiments, the CAR comprises a targeting domain amino acid sequence that is at least 80% identical to that set forth in any one of SEQ ID NOs: 1-4. In certain embodiments, the CAR comprises a targeting domain amino acid sequence that is at least 90% identical to that set forth in any one of SEQ ID NOs: 1-4. In certain embodiments, the CAR comprises a targeting domain amino acid sequence that is at least 95% identical to that set forth in any one of SEQ ID NOs: 1-4. In certain embodiments, the CAR comprises a targeting domain amino acid sequence that is at least 98% identical to that set forth in any one of SEQ ID NOs: 1-4. In certain embodiments, the CAR comprises a targeting domain amino acid sequence that is identical to that set forth in any one of SEQ ID NOs: 1-4.

Preferably, the ECM-specific CAR-expressing T and NK cells have a lower affinity for the ECM of normal (non-malignant) tissues associated with ECM proteins, compared with their affinity for ECM associated with cancer. This can result, for example, because the cancer cells are associated with higher levels of the specific targeted ECM proteins than the normal cells and/or because the extracellular domain of the CARs has higher affinity for the specific form of ECM associated with the cancer cells and/or lower affinity for the specific form of ECM associated with the normal cells. It is preferred that the higher affinity of the CAR-T or NK cells for the cancer ECM is at least 10%, at least 20%, at least 50%, at least 60%, at least 70%, at least 80%, at least 90%, at least 95% or at least 100%, compared with the affinity of the CAR-T or NK cell for the normal ECM. It is preferred that the decrease in affinity of the CAR-T or NK cell for the normal ECM is at least 10%, at least 20%, at least 50%, at least 60%, at least 70%, at least 80%, at least 90%, at least 95% or at least 100%, compared with the affinity of the CAR-T or NK cell for the cancer ECM. It is preferred that the increase in affinity of the CAR-T or NK cell for the cancer ECM is at least 1.5-fold, at least 2-fold, at least 5-fold, at least 10-fold, at least 100-fold, more preferably at least 1000-fold greater than the affinity of the CAR-T or NK cell for the normal ECM.

The transmembrane domain links the extracellular domain and intracellular signal domain. Examples of the transmembrane domain include but are not limited to CD28, CD3-epsilon, CD8-alpha, CD3, CD4, and 4-1BB. Alternatively, a transmembrane domain composed of an artificial polypeptide may be used.

The intracellular signal domain transmits the signals necessary for exertion of the effector function of the T or NK cell. More specifically, when the extracellular domain binds with the target ECM peptide, an intracellular signal domain transmits the signals necessary for activation of the cells. The intracellular signal domain includes the domain for transmitting the signals through for instance the TCR complex, and the domain for transmitting the costimulatory signals. Examples of the costimulatory molecule include CD28, 4-1BB (CD137), CD2, CD4, CD5, CD134, OX-40, and ICOS.

A leader sequence or signal peptide may also be used to promote CAR secretion. For example, the leader sequence of the GM-CSF receptor may be used. In addition, the structure is preferably composed of an extracellular domain and a transmembrane domain linked together through a spacer domain. More specifically, the CAR according to a preferred embodiment contains a spacer domain between the extracellular domain and transmembrane domain. The spacer domain is used for promoting linking between the CAR and target ECM.

The engineered T or NK cells may be bispecific, that is, express bispecific CARs or multiple different CARs, wherein their affinity is for two distinct ligands/antigens. Bispecific CAR-T or NKs can be used either for increasing the number of potential binding sites on cancer cells or in cancer ECM or, alternatively, for localizing cancer cells to other immune effector cells which express ligands specific to the T or NK-CAR. For use in cancer therapy, a bispecific CAR may bind to a target tumor cell or tumor ECM and to an effector cell, e.g. a T cell, NK cell or macrophage. The engineered T or NK cells of the current disclosure may comprise a bispecific CAR or multiple CARs expressed by the same T or NK cell. This allows the T or NK cells to target two different antigens simultaneously.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

Additionally, cytokines and antibody cytokine conjugates can be used therapeutically. Antibodies to the ECM proteins may be used to deliver cytokines which can have a number of functions including enhancing an immune response to the cancerous tissue. Cytokines include but are not limited to IL-2, IL-6, IL-8, IL-10, IL-12, IL-18, TNF, IFN-γ, IFN-β, chemokines, and IFN-α. In one embodiment, the nanobodies can be incorporated into chimeric antigen receptors and then expressed on the surface of T cells (so-called CAR-T cells) to target those cells to the ECM of diseased tissues, thereby enriching them in vicinity of the tumor cells to be targeted.

In one aspect, the invention provides methods for the treatment of other disorders or diseases associated with the abnormal expression of certain ECM protein epitopes. Examples of disorders or diseases associated with the abnormal expression of ECM epitopes include, but are not limited to, cancer, fibrosis, atheromas, inflammatory disorders, and aneurysms.

In one aspect, the invention provides methods for the treatment of cancer. The terms "tumor", "cancer", "cancerous tissue" and "carcinoma" are used interchangeably herein, and each, refers to an uncontrolled growth of cells which interferes with the normal functioning of the bodily organs and systems. Cancers, including those cancers which migrate from their original location and seed vital organs, can eventually lead to the death of the subject through the functional deterioration of the affected organs. Cancers can be classified into a variety of categories including, carcinomas, sarcomas and hematopoietic cancers. Carcinomas are malignant cancers that arise from epithelial cells and include adenocarcinoma and squamous cell carcinoma.

As used herein, a subject is a human, non-human primate, cow, horse, pig, sheep, goat, dog, cat, or rodent. In all embodiments human subjects are preferred. In aspects of the invention pertaining to predictive therapy in cancers, the subject is a human either suspected of having the cancer, or having been diagnosed with cancer. Methods for identifying subjects suspected of having cancer may include physical examination, subject's family medical history, subject's medical history, biopsy, or a number of imaging technologies such as ultrasonography, computed tomography, magnetic resonance imaging, magnetic resonance spectroscopy, or positron emission tomography. Diagnostic methods for cancer and the clinical delineation of cancer diagnoses are well known to those of skill in the medical arts.

Cancer therapies and their dosages, routes of administration and recommended usage are known in the art. In some embodiments, the therapeutic compounds of the invention are formulated into a pharmaceutical composition that further comprises one or more additional anticancer agents.

The active agents of the invention are administered to the subject in an effective amount for treating the subject. An "effective amount", for instance, is an amount necessary or sufficient to realize a desired biologic effect. For instance an effective amount is that amount sufficient to prevent or inhibit cancer cell growth or proliferation or alternatively an amount sufficient to induce apoptosis of a cancer cell or induce tumor regression. In some preferred embodiments the effective amount is that amount useful for reducing the development of metastatic cancers.

The effective amount of a compound of the invention in the treatment of a subject may vary depending upon the specific compound used, the mode of delivery of the compound, and whether it is used alone or in combination. The effective amount for any particular application can also vary depending on such factors as the type and/or degree of cancer in a subject, the particular compound being administered for treatment, the size of the subject, or the severity of the disorder. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity in and of itself and yet is entirely effective to treat the particular subject.

Toxicity and efficacy of the protocols of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays, animal studies and human studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

As used herein, the term "treat", "treated", or "treating" when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

The diagnostic and therapeutic compounds described herein can be administered in combination with other therapeutic agents and such administration may be simultaneous or sequential. When the other therapeutic agents are administered simultaneously they can be administered in the same or separate formulations, but are administered at the same time. The administration of the other therapeutic agent, including chemotherapeutics can also be temporally separated, meaning that the therapeutic agents are administered at a different time, either before or after, the administration of the therapeutics described herein. The separation in time between the administration of these compounds may be a matter of minutes or it may be longer. When used in combination with the therapies of the invention the dosages of known therapies may be reduced in some instances, to avoid side effects.

Thus, in some instances, the invention also involves administering another cancer treatment (e.g., radiation therapy, chemotherapy or surgery) to a subject. Examples of conventional cancer therapies include treatment of the cancer with agents such as All-trans retinoic acid, Actinomycin D, Adriamycin, anastrozole, Azacitidine, Azathioprine, Alkeran, Ara-C, Arsenic Trioxide (Trisenox), BiCNU Bleomycin, Busulfan, CCNU, Carboplatin, Capecitabine, Cisplatin, Chlorambucil, Cyclophosphamide, Cytarabine, Cytoxan, DTIC, Daunorubicin, Docetaxel, Doxifluridine, Doxorubicin, 5-flurouracil, Epirubicin, Epothilone, Etoposide, exemestane, Erlotinib, Fludarabine, Fluorouracil, Gemcitabine, Hydroxyurea, Herceptin, Hydrea, Ifosfamide, Irinotecan, Idarubicin, Imatinib, letrozole, Lapatinib, Leustatin, 6-MP, Mithramycin, Mitomycin, Mitoxantrone, Mechlorethamine, megestrol, Mercaptopurine, Methotrexate, Mitoxantrone, Navelbine, Nitrogen Mustard, Oxaliplatin, Paclitaxel, pamidronate disodium, Pemetrexed, Rituxan, 6-TG, Taxol, Topotecan, tamoxifen, taxotere, Teniposide, Tioguanine, toremifene, trimetrexate, trastuzumab, Valrubicin, Vinblastine, Vincristine, Vindesine, Vinorelbine, Velban, VP-16, and Xeloda.

Multiple doses of the molecules of the invention are also contemplated. In some instances, when the molecules of the invention are administered with another therapeutic, for instance, a chemotherapeutic agent a sub-therapeutic dosage of either or both of the molecules may be used. A "sub-therapeutic dose" as used herein refers to a dosage which is less than that dosage which would produce a therapeutic result in the subject if administered in the absence of the other agent.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The compounds may be sterile or non-sterile.

The compounds described herein may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. In general, a pharmaceutical composition comprises the compound of the invention and a pharmaceutically acceptable carrier. Pharmaceutically acceptable carriers for nucleic acids, small molecules, peptides, monoclonal antibodies, and antibody fragments are well-known to those of ordinary skill in the art. As used herein, a pharmaceutically acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants, including those designed for slow or controlled release.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In one embodiment the disclosure provides a method of treating a patient having a solid tumor by administering a CAR-T cell expressing a CAR. In another embodiment, the disclosure provides a method of recruiting immune cells to a solid tumor in a patient by administering a CAR-T cell expressing a CAR. In some instances, the CAR-T cells can be administered using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient. In another embodiment, the disclosure provides a method of recruiting immune cells to a solid tumor in a patient by administering an anti-ECM nanbody coupled to a cytokine or other binding agent that recruits immune cells.

The invention also includes kits made up of the various reagents described herein assembled to accomplish the methods of the invention. A kit for instance may include one or more reagents for detecting one or more ECM protein epitopes, such as the EIIIB domain of FN and/or TNC. The kit may further comprise assay diluents, standards, controls and/or detectable labels. The assay diluents, standards and/or controls may be optimized for a particular sample. Binding peptide or polypeptides include, for instance, nanobodies, antibodies, nucleic acids, labeled secondary agents. One skilled in the art will readily recognize that reagents of the present invention can be readily incorporated into one of the established kit formats which are well known in the art.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment or characterization of a cancer.

"Instructions" can define a component of promotion, and typically involve written instructions on or associated with packaging of compositions of the invention. Instructions also can include any oral or electronic instructions provided in any manner.

Thus, the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Extracellular Matrix Enrichment and LC/MS

Lung and liver metastases of patients with triple-negative breast cancer (TNBC) and liver metastases from patients with colorectal cancer were obtained. Using methods previously described, the samples were enriched for the ECM of these tissues (Naba et al., Mol Cell Proteomics. 11:M111 014647 (2012). A portion of the ECM preparations was subjected to LC-MS/MS analysis and the remainder was used to immunize alpacas for the purpose of nanobody library generation using established methods (Pardon et al., Nat Protoc. 9(3): 674-93 (2014).

Example 2

Alpaca Immunization

The extracellular matrix of diseased tissues is known to be distinct from that of normal tissue and often contains ECM proteins and epitopes of ECM proteins that are exclusively or selectively present at diseased sites (as shown by LC/MS/MS and confirmed by immunohistochemistry). To develop alpaca-derived nanobodies specific for ECM protein epitopes associated with diseased tissues like cancer, four different alpacas were immunized with the following: (a) a cocktail of ECM proteins and synthetic peptides from proteins associated with diseased ECM; (b) ECM preparations from human patient colon cancer metastases to the liver; (c) ECM preparations from human patient triple-negative breast cancer metastases to the liver; and (d) ECM preparations from human patient triple-negative breast cancer metastases to the lung.

Example 3

Nanobody Library Construction

Camelidae such as alpacas, in addition to making conventional immunoglobulin, also make heavy-chain-only antibodies, which bind their antigen through their VHH (variable region of the heavy chain of the heavy-chain-only antibody) domains. Recombinant VHH domains are called Nanobodies, which are single-domain antibodies containing the entire specificity of the intact antibody in a single protein domain of 15 kDa. Lymphocytes were isolated from blood collected from alpacas immunized and boosted with ECM preparations. The lymphocyte RNA was extracted and cDNA encoding VHH domains was amplified by PCR and used for the construction of M13 phage-display-based nanobody libraries. Four M13 libraries were generated against the extracellular matrix protein preparations described above. The libraries are shown in Table 1. These libraries had a diversities of $10^5$-$10^6$ cfu/ml.

TABLE 1

| Library | Immunogen | Diversity |
|---|---|---|
| A | Cocktail of ECM proteins and synthetic peptides derived from ECM proteins associated with diseased ECM | $10^5$/ml |
| B | ECM preparations from human patient colorectal cancer metastases to the liver | $10^6$/ml |
| C | ECM preparations from human patient triple negative breast cancer metastases to the liver | $10^6$/ml |
| D | ECM preparations from human patient triple negative breast cancer metastases to the lungs | $10^6$/ml |

Example 4

Development and Application of the Nanobodies against the EIIIB Domain of Fibronection 4.1 Panning for Nanobodies against the EIIIB Domain of Fibronectin Fibronectin (FN) is a large multifunctional glycoprotein, which forms a major component of the extracellular matrix (ECM) of tissues (Hynes, Annu Rev Cell Biol. 1:67-90 (1985; Hynes 1990). FN undergoes alternative splicing during embryonic development, wound healing, tissue repair, fibrosis, cardiovascular disease, angiogenesis and tumor formation. This alternative splicing leads to the inclusion of domains EIIIA and EIIIB in disease ECM, but not in normal ECM (White and Muro, JUBMB Life, 63(7): 538-46 (2011)). The expression of these domains in disease ECM, and their absence from normal tissue and plasma, makes them promising targets for nanobody-based imaging and therapeutics.

Figures 1A, 1B:
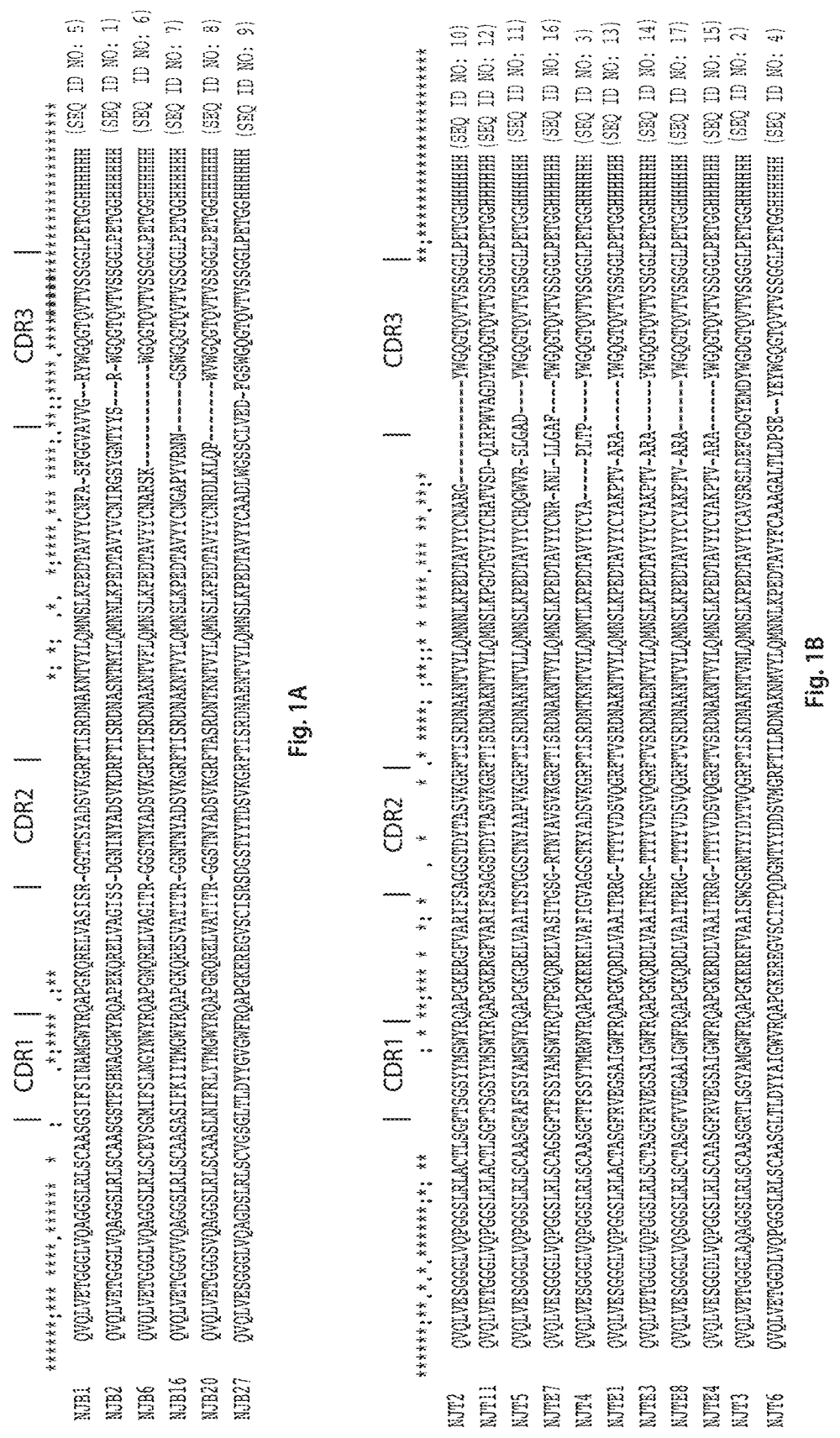

The A library was used to pan nanobodies specific for recombinantly expressed EIIIB domain of FN using established phage display panning methods. Based on the sequence diversity in the CDR3 (complementarity determining region 3), six unique clones were isolated from the panning, the sequences of which are shown in FIG. 1A and Table 2. The CDRs are presented in Table 3. These clones were processed to express the encoded VHH nanobodies and tested for their specificity for an epitope in the EIIIB domain using various in vitro assays including immunoblotting, ELISA, immunofluorescence and immunohistochemistry. FIG. 2 demonstrates the specificity of clone NJB2 for an epitope in the EIIIB domain.

Figure 3:
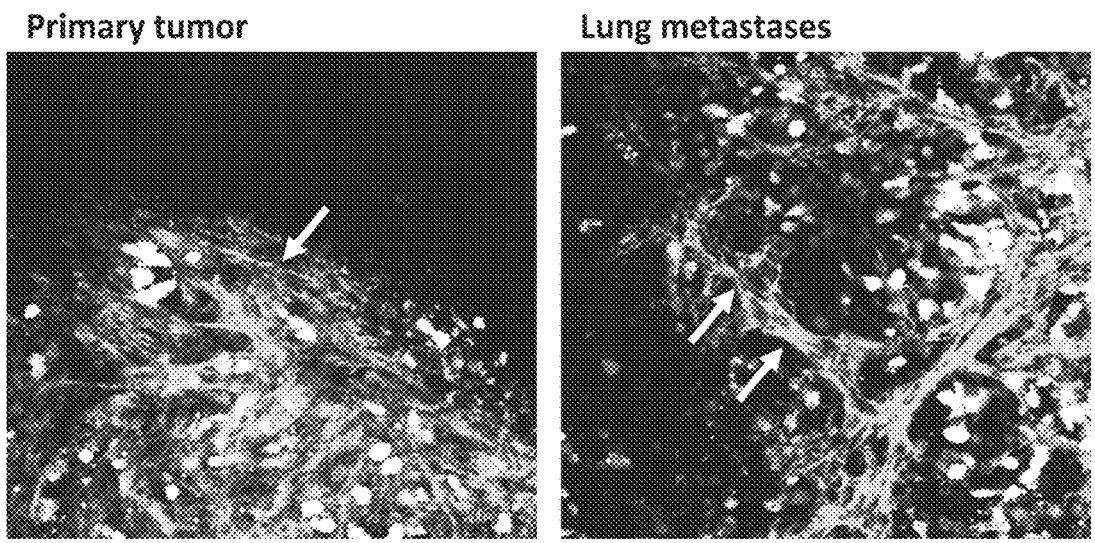
FIG. 3 shows that VHH NJB2 specifically recognizes tumor ECM. NJB2 was site-specifically labelled with Texas Red via sortagging and introduced into mice to label the tumor ECM. The images were acquired using ex vivo two-photon microscopy of the dissected tumors and show an overlay of the different channels. The cells (green in the originals) appear as round white objects; the ECM (Texas Red stained) appears as fibrils. The left panel shows an image of an orthotopically transplanted LM2-Zs-Green-Luciferase tumor grown in a NOD-SCID Gamma (NSG) mouse subsequently injected with 20 ug of NJB2-Texas red, 120 minutes prior to imaging. The right panel shows an image of lung metastases of LM2-Zs-Green-Luciferase tumors visualized in a NSG mouse injected with 20 ug of NJB2-Texas red, 120 minutes prior to imaging. In both cases, the ECM fibers (arrows) bound by the nanobodies can be clearly seen surrounding tumor cells.
Figures 4A, 4B:
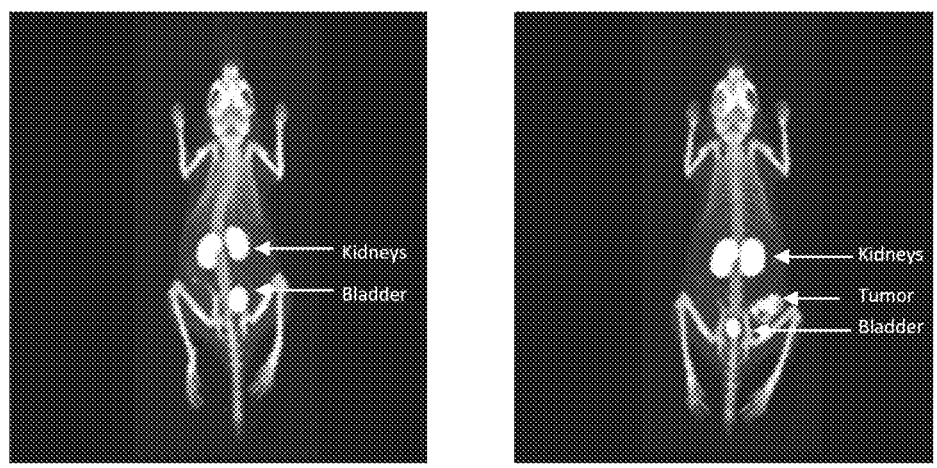
FIGS. 4A-4C show that $^{64}$Cu-NJB2 detects orthotopic primary tumors and lung metastases derived from LM2 TNBC human cell line. VHH-NJB2 was site-specifically labelled with $^{64}$Cu using sortagging. Mice were imaged 2 h post injection of $^{64}$Cu-NJB2.
Figure 4C:
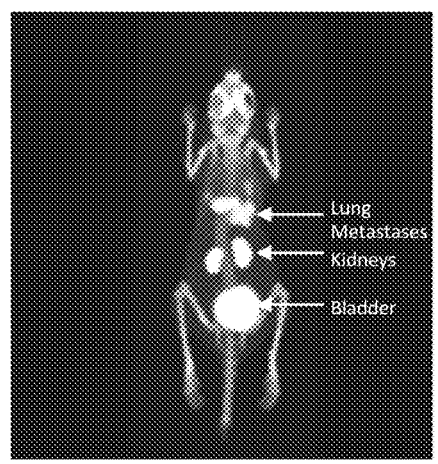
Figure 5A:
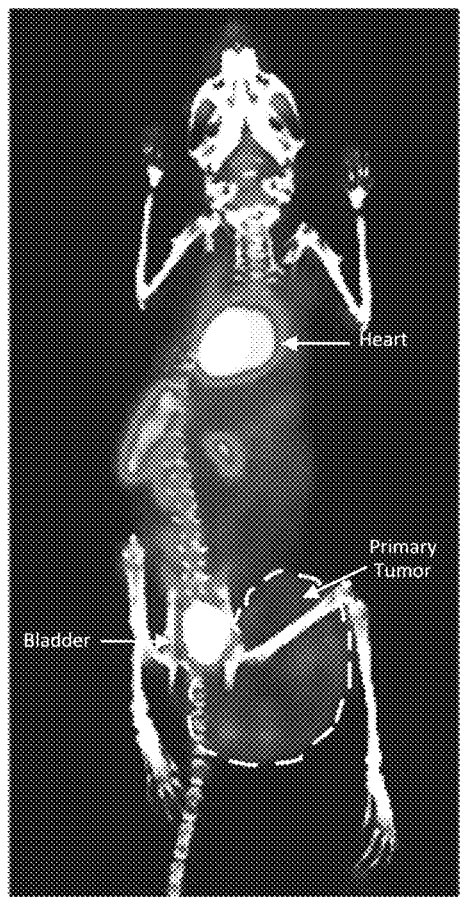
FIGS. 5A-5B show that $^{64}$Cu-NJB2 detects primary tumor and metastases to the liver and lymph node in a mouse orthotopically seeded in the mammary gland with LM2 TNBC human mammary carcinoma cells. VHH-NJB2 was site-specifically labelled with $^{64}$Cu using sortagging. $^{64}$Cu-NJB2 immuno-PET/CT images were compared with $^{18}$F-FDG images of the same mouse. NSG mice with orthotopic (mammary fat pad) tumors derived from LM2-ZsGreen-Luciferase TNBC cells were injected with $^{18}$F-FDG (FIG.
Figure 5B:
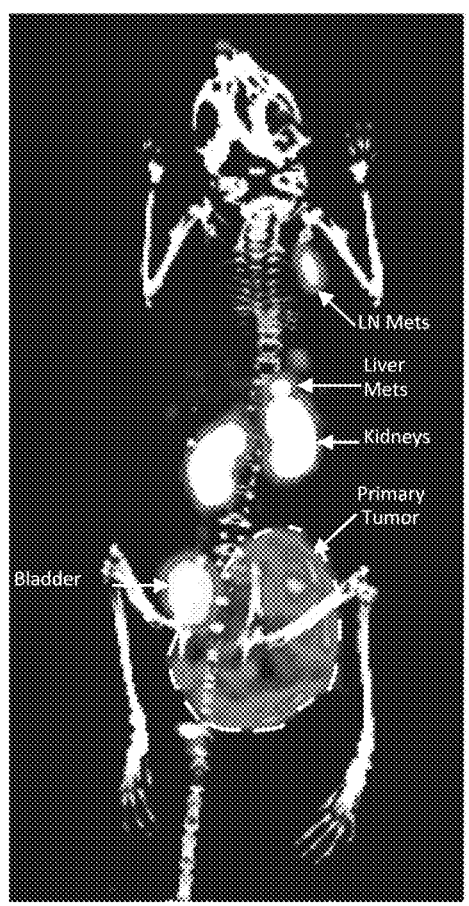

To test further the specificity and binding of NJB2 to EIIIB expressed in tumors and metastatic sites, ex vivo fluorescence imaging using 2-photon microscopy was performed and NJB2 was found to localize specifically to the tumor ECM (FIG. 3). In vivo binding was further tested by immuno-PET/CT with $^{64}$Cu-labeled NJB2 injected into tumor-bearing mice. The NJB2 nanobody localized specifically to tumor ECM with a high signal-to-background ratio (FIGS. 4A-4C). To compare the specificity of binding to tumor ECM and the sensitivity of detecting small metastases, the NJB2 immuno-PET images were compared with $^{18}$F-FDG images on the same mice. The NJB2 immuno-PET could successfully detect orthotopic metastases (2-4 mm in diameter) to the liver and lymph node (FIG. 5B), neither of which were clearly detected by $^{18}$F-FDG PET (FIG. 5A). Note that the tumors and metastases in this and subsequent examples and figures are much more readily observed in the original colored images and movies from which these figures were derived.

4.2: $^{64}$Cu-NJB2 Nanobody in Early Detection of Pancreatic Ductal Adenocarcinoma Pancreatic ductal adenocarcinoma (PDAC) develops through well-defined neoplastic stages and is characterized by increasing desmoplasia and prominent ECM deposition. PDAC progression from initiation to metastatic disease can take nearly 2 decades, suggesting a wide window of opportunity for early detection. We were interested in testing whether NJB2 can be used for early detection and tracking of PDAC progression. We used the KPC mouse models of PDAC which recapitulate different stages of PDAC progression including pancreatic intraepithelial neoplasias (PanINs), which are precursor lesions that later progress to PDAC. To test the expression of EIIIB during PDAC progression, we observed EIIIB expression in the stroma of PanIN lesions and very strong EIIIB staining in the PDAC stroma, whereas no EIIIB was detected in normal pancreas. These results indicated increasing inclusion/expression of FN containing EIIIB during PDAC progression in mice. Furthermore, IHC with NJB2-biotin on tissue sections of human PDAC patient samples showed that the nanobody binds to the EIIIB expressed in human PDAC stroma. To test the binding of NJB2 to PDAC tumors in vivo, 2-8-month-old KPC mice were injected via tail vein with $^{64}$Cu-NJB2 and imaged with PET/CT 2 hours later. In mice with PDAC imaged with $^{64}$Cu-NJB2 PET/CT, the nanobody bound specifically to large pancreatic tumors (FIG. 6B). In mice with PanINs imaged with $^{64}$Cu-NJB2 PET/CT, a distinct PET signal was evident in the region of the pancreas (FIG. 6D); this is a particular example of images that are much clearer in color and in 3-D reconstruction videos. The same mice were also imaged with $^{18}$F-FDG for comparison. While the large pancreatic tumors were detected by $^{18}$F-FDG (FIG. 6A), the PanIN lesions were not clearly visible with $^{18}$F-FDG PET/CT imaging (FIG. 6C). NJB2 can thus be used for noninvasive early detection and screening of PDAC and also for monitoring PDAC progression with high specificity and sensitivity.

4.3: $^{64}$Cu-NJB2 Detects Tumors and Metastases in Syngeneic Models of Melanoma and Triple-Negative Breast Cancer We next explored whether the NJB2 nanobody can target and detect tumors and metastases in immuno-competent syngeneic models of breast cancer (4T1 in BALB/c) and melanoma (B16F10 in C57BL/6). The 4T1 tumors are a model of triple-negative breast cancer, which can spontaneously metastasize to distant sites, including lung, liver and lymph nodes. Mice bearing syngeneic primary tumors or pulmonary metastases were further imaged with $^{64}$Cu-NJB2 PET/CT, which detected the tumors and lung metastases with high specificity in both models (FIG. 7A and 7B, more readily visualized in color).

4.4: Noninvasive Detection and Tracking of Pulmonary Fibrosis with Cu-NJB2

Fibrosis is characterized by the excessive deposition of ECM containing fibronectin. The expression of FN containing EIIIB/EIIIA is low/absent in normal tissues but high in sites of fibrosis. Bleomycin has been used widely to induce experimental lung fibrosis mimicking many aspects of clinical pulmonary fibrosis. Bleomycin- and sham-treated mice were imaged with $^{64}$Cu-NJB2 immuno-PET/CT. The nanobody bound to regions of fibrotic lung, showing distinct signals in the lungs at both day 7 and 14 after bleomycin treatment (FIG. 8). We conclude that $^{64}$Cu-NJB2 detects pulmonary fibrosis noninvasively with excellent specificity and a high signal-to-noise ratio.

4.5: $^{64}$Cu-NJB2 Detects Tumor Progression in Breast Cancer

Non-invasive monitoring of disease progression (such as in response to therapy) is an important application of in vivo imaging. To assess whether $^{64}$Cu-NJB2 could be a useful tool in this application we chose the MMTV-PyMT model of breast cancer progression, in which mice develop spontaneous autochthonous tumors. This model recapitulates many aspects of human breast cancer progression. Tumor progression occurs via 4 distinct stages; hyperplasia (4-6 weeks of age), premalignant adenoma (8-9 weeks of age), early carcinoma (malignant transition at 8-12 weeks of age) which then progresses into advanced carcinoma. We used longitudinal immuno-PET/CT imaging to monitor tumor progression. MMTV-PyMT females (n=7) were imaged with $^{64}$Cu-NJB2 PET/CT from 6 weeks to 13 weeks. PET signals from mammary fat-pad tumors were detected in 10-week-old mice. As tumor growth progressed from week 10 to week 13, PET signals were observed from multiple macroscopic tumor nodules in all mice (FIG. 9). Based on immunohistochemistry, this model expresses lower levels of EIIIB compared to the other breast cancer models tested. NJB2 can thus be used to target and monitor tumor progression even in mouse models that express low levels of EIIIB.

4.6: FN-EIIIB is widely expressed in metastases derived from multiple cancer types Having demonstrated that the nanobody can detect small metastases, which remains technically challenging using conventional imaging such as $^{18}$F-FDG PET/CT, we wanted to assess how broadly NJB2 can be used for the detection and targeting of metastases. To investigate the expression of EIIIB in metastasis samples from multiple patients, we stained a multi-organ tissue array of samples from various metastatic sites derived from 104 patients with NJB2-biotin. Tissues were scored for EIIIB signal in the ECM and we found that in the tissue array stained with NJB2-biotin, ~44% of the patients expressed FN-EIIIB at their metastatic sites (FIG. 10). In parallel, similar results were obtained with a monoclonal anti-EIIIB antibody (AM3, data not shown). These metastases to multiple organs (21 distinct sites) were derived from 17 different primary sites, including rectum, pancreas, lung, ovary, stomach and thyroid among others (Table 4). Among the EIIIB-positive biopsies, ~32% were metastases to the lymph nodes at the metastatic sites (Table 4). This wide expression of EIIIB at metastatic sites in multiple organs and derived from multiple types of primary tumors further broadens the potential applications of NJB2-based imaging and therapeutic applications.

TABLE 4

| Primary site | Both positive | Single positive | Metastatic site(s) | | |
|---|---|---|---|---|---|
| Thyroid | 4 | 1 | Neck (9) | | |
| Endometrium | 3 | | Vaginal wall (2) | Abdominal cavity (2) | Pelvic cavity (2) |
| Lung | 3 | | Left frontal lobe (4) | Mediastinum (2) | |
| Ovary | 2 | 2 | Omentum (1) | Peritoneum (3) | Appendix (2) |
| Cervix | 2 | 1 | Colon (2) | Abdominal wall (2) | Pelvic cavity (1) |
| Bladder | 2 | 2 | Penis (1) | Back (2) | Pelvic cavity (3) |
| Kidney | 2 | | Adrenal gland (2) | Renal Hilum (2) | |
| Oesophagus | 2 | | Around oesophagus (2) | Mediastinum (2) | |
| Rectum | 2 | 2 | Ovary (3) | Liver (3) | |
| Duodenum | 2 | | Mesentry (2) | Omentum (2) | |
| Stomach | 2 | 1 | Omentum (4) | Cardia (1) | |
| Penis | 1 | | Groin (2) | | |
| Larynx | 1 | 1 | Neck (3) | | |
| Colon | 1 | 1 | Mesentry (2) | Liver (1) | |
| Skin | 1 | | Occipital lobe (2) | | |
| Pancreas | | 4 | Omentum (2 + 2) | | |
| Vulva | | 1 | Groin (1) | | |

Example 5

Panning for Nanobodies against Human Tenascin C

Tenascin C (TNC) is a large ECM protein that is largely absent in adult human tissues (with the exception of low levels of expression in tendons and ligaments and the sub-ventricular zone of the CNS) (Giblin and Midwood, Cell Adh Migr. 9: 48-82 (2015)). However, the protein is specifically re-expressed in diseased tissues associated with ECM remodeling such as sites of inflammation and cancer. Its restricted pattern of expression in activated stroma/disease-associated ECM makes it an attractive target for nanobody-based imaging and therapeutic approaches (Giblin and Midwood, Cell Adh Migr. 9: 48-82 (2015); Gocheva et al, 2017)).

The libraries B and C depicted in Table 1 were used to pan for nanobodies specific for human tenascin C. Eleven unique clones (based on overall sequence diversity) were isolated, out of which eight were unique based on their CDR3 region, the sequences of which are shown in FIG. 1B and Table 2. The CDRs are presented in Table 3. These clones were expressed, and subsequently tested for their specificity for tenascin C using various in vitro assays including immunoblotting, ELISA and immunohistochemistry. FIG. 11 depicts three nanobodies (NJT3, NJT4 and NJT6) specific for human tenascin C protein in ELISA assay. These nanobodies were found to bind specifically to tenascin C in tumor ECM (FIG. 12).

To test further the specificity and binding of VHHs to tenascin C expressed in tumors, NJT3, NJT4 and NJT6 were site-specifically labelled with Texas Red via sortase-mediated tagging. Ex vivo fluorescence imaging using 2-photon microscopy was performed and VHHs to tenascin C was found to localize specifically to the tumor ECM (FIG. 13). In vivo binding was further tested by immuno-PET/CT with $^{64}$Cu-labeled NJT6 injected into NGS mice bearing tumors and metastases derived from LM2 TNBC cells. The NJT6 nanobody localized specifically to tumors and lung metastases with a high signal-to-background ratio (FIGS. 14 A,B).

Example 6

Nanobody-based CAR-T Cells Suppress Tumor Growth and Recruit T cells

Despite its success in treating hematological cancers, solid tumors are not so easily eliminated by chimeric antigen receptor (CAR) T cell therapy. Solid tumors generally develop in a highly immunosuppressive environment and are difficult to target, mostly due to a lack of tumor-specific antigen expression, but other factors contribute as well. The use of single domain antibody (VHH)-based CAR-T cells that recognize these markers circumvents the need for tumor-specific targets on the cancer cells themselves. VHH-based CAR-T cells that target the tumor microenvironment through stroma and ECM markers are effective against solid tumors in syngeneic, immunocompetent animal models.

The VHH-based CART cells generated in this study follow the principal design of scFv-based CAR-T cells, where the T cells are transduced by lentiviral vector encoding the recognition module in chimera with transmembrane and signaling domains. In this case, VHH replaced the scFv as the recognition module. We used VHHs specific for the EIIIB splice variant of fibronectin (NJB2) to generate a CAR construct by standard methods used in the field. A lentiviral vector backbone derived from murine stem cell virus encoding the CAR construct in addition to an IRES-driven fluorescent marker cassette to gauge transduction efficiency was used to transduce mouse T cells so that they expressed the NJB2 CAR on their surfaces to generate CAR-T cells specific to the tumor microenvironment (B2 CAR-T cells hereafter).

Having confirmed the binding specificity of B2 CAR-T cells to EIIIB, we used the B 16F10 melanoma model to show that treatment with B2 CAR-T cells delays tumor growth. Mice were injected subcutaneously with $1 \times 10^5$ B16F10 melanoma cells and B2 CAR-T cell injections ($1 \times 10^7$-$1.5 \times 10^7$ cells) were given 4 days and 11 days post B 16F10 cell injection. Tumors were harvested at day 16 and tumor size was measured and graphed as tumor area. The B2 CAR-T cells successfully delayed tumor growth (FIG. 15A). B2 CAR-T cell treatment was also tested in a B16 model in immunocompromised RAG-/- mice to determine the contribution of the endogenous adaptive immune system in the efficacy of treatment. We saw no significant increase in survival or delay in tumor growth when tumor-bearing mice lacking adaptive immunity were treated with the B2 CAR-T cells, despite efficient expansion of the B2 CAR-T cells, indicating that the CAR treatment synergizes with the endogenous adaptive immune system to show efficacy in these immunocompetent tumor models (data not shown). These results show that targeting CAR-T cells selectively to tumor ECM and neovasculature can be very effective in suppressing tumor growth. We conclude that we can apply VHHs to generate CAR-T cells that are effective in vivo against targets in the tumor microenvironment in fully immunocompetent mice.

To more closely analyze the mechanisms of B2 CAR-T cell treatment, we performed immunohistochemistry (IHC) on tumors excised while undergoing treatment. Wild-type C57BL/6 mice were inoculated with B16F10 tumors, and mice were either treated with B2 CAR-T cells or left untreated. At day 16, when there was a significant difference in tumor sizes between the treated and control group (FIG. 15A), tumors were excised, fixed, and subjected to IHC. Tumor samples were then stained for CD31, CD3, CD4 and CD8 to determine how vasculature and immune cell populations were affected by the B2 CAR-T cell treatment. The structure of the untreated tumors appeared healthy and intact, while the treated tumors showed clear signs of disruption. The treated samples showed decreased levels of CD31-positive vasculature compared to controls. Since B2 CAR-T cells are targeted to EIIIB, which is expressed in tumor stroma and on neovasculature, the necrotic nature and lack of CD31 expression in the treated samples is perhaps to be expected. Averaging across all tumors, those treated with B2 CAR-T cells had elevated levels of T-cells, as evidenced by increased staining of CD3, CD4 and CD8 compared to untreated tumors (FIG. 15B). The infiltrated T cells were quantified in FIG. 15C. A reasonable interpretation is that the B2 CAR-T cells infiltrate the tumors and possibly also recruit additional immune cells. These data further corroborate the ability of B2-CAR-T cells to infiltrate and damage EIIIB-expressing tumors. Tumors rely on support and nutrients delivered by their stroma and vasculature, and by compromising these interactions, the B2 CAR-T cells markedly delay tumor growth.

TABLE 2

Sequences of Nanobodies

| Name | Sequence | SEQ ID NO: |
|---|---|---|
| EIIIB Nanobodies | | |
| NJB1 | QVQLVETGGGLVQAGGSLRLSCAAS<u>GSIFSINAMG</u>WYRQAPGKQRELV<u>ASISRGG TTSYAD</u>SVKGRFTISRDNAKNTVYLQMNSLKPEDTAVYY<u>CNFASFGGVAVVGRY WG</u>QGTQVTVSSGGLPETGGHHHHHH | 5 |
| NJB2 | QVQLVETGGGLVQAGGSLRLSCAAS<u>GSTFSHNAGG</u>WYRQAPEKQRELV<u>AGISSD GNINYAD</u>SVKDRFTISRDNASNTMYLQMNNLKPEDTAVYY<u>CNIRGSYGNTYYSR WG</u>QGTQVTVSSGGLPETGGHHHHHH | 1 |
| NJB6 | QVQLVETGGGLVQAGGSLRLSCEVS<u>GMIFSLNGYN</u>WYRQAPGNQRELV<u>AGITRG GSTNYAD</u>SVKGRFTISRDNAKNTVFLQMNSLKPEDTAVYY<u>CNARSKW</u>GQGTQVT VSSGGLPETGGHHHHHH | 6 |
| NJB16 | QVQLVETGGGVVQAGGSLRLSCAAS<u>ASIFKIITMG</u>WYRQAPGKQRESV<u>ATITRGG NTNYAD</u>SVKGRFTISRDNAKNTVYLQMNSLKPEDTAVYY<u>CNGAPYVRNNGSWG</u> QGTQVTVSSGGLPETGGHHHHHH | 7 |
| NJB20 | QVQLVETGGGSVQAGGSLRLSCAAS<u>LNIFRLYTMG</u>WYRQAPGRQRELV<u>ATITRGG STNYAD</u>SVKGRFTASRDNTKNTVYLQMNSLKPEDTAVYY<u>CNRDLKLQPWVWGQ</u> GTQVTVSSGGLPETGGHHHHHH | 8 |
| NJB27 | QVQLVESGGGLVQAGDSLRLSCVG<u>SGLTLDYYGVGW</u>FRQAPGKEREGV<u>SCISRSD GSTYYTD</u>SVKGRFTISRDNAENTVYLQMNSLKPEDTAVYY<u>CAADLWGSSCLVEDF GSW</u>GQGTQVTVSSGGLPETGGHHHHHH | 9 |
| Tenascin C Nanobodies | | |
| NJT2 | QVQLVESGGGLVQPGGSLRLACTL<u>SGFTSGSYYMS</u>WYRQAPGKERGFV<u>ARIFSAG GSTDYTA</u>SVKGRFTISRDNAKNTVYLQMNNLKPEDTAVYY<u>CNARGYW</u>GQGTQV TVSSGGLPETGGHHHHHH | 10 |
| NJT3 | QVQLVETGGGLAQAGGSLRLSCAAS<u>GRTLSGYAMG</u>WFRQAPGKEREFV<u>AAISWS GRNTYYDY</u>TVQGRFTISKDNAKNTVNLQMNSLKPEDTAVYY<u>CAVSRSLDEFGDG YEMDYW</u>GDGTQVTVSSGGLPETGGHHHHHH | 2 |
| NJT4 | QVQLVESGGGLVQPGGSLRLSCAAS<u>GFTFSSYTMR</u>WYRQAPGKERELV<u>AFIGVAG GSTKYAD</u>SVKGRFTISRDNTKNTVYLQMNTLKPEDTAVYY<u>CYAPLTPYW</u>GQGTQ VTVSSGGLPETGGHHHHHH | 3 |
| NJT5 | QVQLVESGGGLVQPGGSLRLSCAAS<u>GFAFSSYAMS</u>WYRQAPGKGRELV<u>AAITSTG GSTNYAAP</u>VKGRFTISRDNAKNTVLLQMNSLKPEDTAVYY<u>CHQGWVRSLGADY WG</u>QGTQVTVSSGGLPETGGHHHHHH | 11 |
| NJT6 | QVQLVETGGDLVQPGGSLRLSCAAS<u>GLTLDYYAIGW</u>VRQAPGKEREGV<u>SCITPQD GNTYYDDS</u>VMGRFTILRDNAKNMVYLQMNNLKPEDTAVYF<u>CAAAGALTLDPSE YEYW</u>GQGTQVTVSSGGLPETGGHHHHHH | 4 |
| NJT11 | QVQLVETGGGLVQPGGSLRLACTL<u>SGFTSGSYYMS</u>WYRQAPGKERGFV<u>ARIFSAG GSTDYTA</u>SVKGRFTISRDNAKNTVYLQMNSLKPGDTGVYY<u>CHATVSDQIRPWVA GDYW</u>GQGTQVTVSSGGLPETGGHHHHHH | 12 |

TABLE 2-continued

Sequences of Nanobodies

| Name | Sequence | SEQ ID NO: |
|---|---|---|
| NJTE1 | QVQLVESGGGLVQPGGSLRLACTA<u>SGFRVEGSAIG</u>WFRQAPGKQRDLV<u>AAITRRG TTTYVD</u>SVQGRFTVSRDNAKNTVYLQMNSLKPEDTAVYY<u>CYAKPTVARAYW</u>GQ GTQVTVSSGGLPETGGHHHHHH | 13 |
| NJTE3 | QVQLVETGGGLVQPGGSLRLSCTA<u>SGFRVEGSAIG</u>WFRQAPGKQRDLV<u>AAITRRG TTTYVD</u>SVQGRFTVSRDNAENTVYLQMNSLKPEDTAVYY<u>CYAKPTVARAYW</u>GQ GTQVTVSSGGLPETGGHHHHHH | 14 |
| NJTE4 | QVQLVESGGDLVQPGGSLRLSCAA<u>SGFRVEGSAIG</u>WFRQAPGKERDLV<u>AAITRRG TTTYVD</u>SVQGRFTVSRDNAKNTVYLQMNSLKPEDTAVYY<u>CYAKPTVARAYW</u>GQ GTQVTVSSGGLPETGGHHHHHH | 15 |
| NJTE7 | QVQLVESGGGLVQPGGSLRLSCAG<u>SGFTFSSYAMS</u>WYRQTPGKQRELV<u>ASITGSG RTNYAV</u>SVKGRFTISRDNAKNTVYLQMNSLKPEDTAVYY<u>CNRKNLLLGAFTW</u>GQ GTQVTVSSGGLPETGGHHHHHH | 16 |
| NJTE8 | QVQLVESGGGLVQSGGSLRLSCTA<u>SGFVVEGAAIG</u>WFRQAPGKQRDLV<u>AAITRRG TTTYVD</u>SVQGRFTVSRDNAKNTVYLQMNSLKPEDTAVYY<u>CYAKPTVARAYW</u>GQ GTQVTVSSGGLPETGGHHHHHH | 17 |

TABLE 3

CDRs of Nanobodies

| Construct | CDR1 | CDR2 | CDR3 |
|---|---|---|---|
| NJB1 | GSIFSINAMG (SEQ ID NO. 18) | ASISRGGTTSYAD (SEQ ID NO. 35) | CNFASFGGVAVVGRYW (SEQ ID NO. 52) |
| NJB2 | GSTFSHNAGG (SEQ ID NO. 19) | AGISSDGNINYAD (SEQ ID NO. 36) | CNIRGSYGNTYYSRW (SEQ ID NO. 53) |
| NJB6 | GMIFSLNGYN (SEQ ID NO. 20) | AGITRGGSTNYAD (SEQ ID NO. 37) | CNARSKW (SEQ ID NO. 54) |
| NJB16 | SASIFKIITMG (SEQ ID NO. 21) | ATITRGGNTNYAD (SEQ ID NO. 38) | CNGAPYVRNNGSW (SEQ ID NO. 55) |
| NJB20 | SLNIFRLYTMG (SEQ ID NO. 22) | ATITRGGSTNYAD (SEQ ID NO. 39) | CNRDLKLQPWVW (SEQ ID NO. 56) |
| NJB27 | SGLTLDYYGVG (SEQ ID NO. 23) | SCISRSDGSTYYTD (SEQ ID NO. 40) | CAADLWGSSCLVEDFGSW (SEQ ID NO. 57) |
| NJT2 | SGFTSGSYYMS (SEQ ID NO. 24) | ARIFSAGGSTDYTA (SEQ ID NO. 41) | CNARGYW (SEQ ID NO. 58) |
| NJT3 | SGRTLSGYAMG (SEQ ID NO. 25) | AAISWSGRNTYYDY (SEQ ID NO. 42) | CAVSRSLDEFGDGYEMDYW (SEQ ID NO. 59) |
| NJT4 | SGFTFSSYTMR (SEQ ID NO. 26) | AFIGVAGGSTKYAD (SEQ ID NO. 43) | CYAPLTPYW (SEQ ID NO. 60) |
| NJT5 | SGFAFSSYAMS (SEQ ID NO. 27) | AAITSTGGSTNYAA (SEQ ID NO. 44) | CHQGWVRSLGADYW (SEQ ID NO. 61) |
| NJT6 | SGETEDYYAIG (SEQ ID NO. 28) | SCITPQDGNTYYDD (SEQ ID NO. 45) | CAAAGALTLDPSEYEYW (SEQ ID NO. 62) |
| NJT11 | SGFTSGSYYMS (SEQ ID NO. 29) | ARIFSAGGSTDYTA (SEQ ID NO. 46) | CHATVSDQIRPWVAGDYW (SEQ ID NO. 63) |
| NJTE1 | SGFRVEGSAIG (SEQ ID NO. 30) | AAITRRGTTTYVD (SEQ ID NO. 47) | CYAKPTVARAYW (SEQ ID NO. 64) |
| NJTE3 | SGFRVEGSAIG (SEQ ID NO. 31) | AAITRRGTTTYVD (SEQ ID NO. 48) | CYAKPTVARAYW (SEQ ID NO. 65) |
| NJTE4 | SGFRVEGSAIG (SEQ ID NO. 32) | AAITRRGTTTYVD (SEQ ID NO. 49) | CYAKPTVARAYW (SEQ ID NO. 66) |

TABLE 3-continued

| | CDRs of Nanobodies | | |
|---|---|---|---|
| Construct | CDR1 | CDR2 | CDR3 |
| NJTE7 | SGFTFSSYAMS (SEQ ID NO. 33) | ASITGSGRTNYAV (SEQ ID NO. 50) | CNRKNLLLGAFTW (SEQ ID NO. 67) |
| NJTE8 | SGFVVEGAAIG (SEQ ID NO. 34) | AAITRRGTTTYVD (SEQ ID NO. 51) | CYAKPTVARAYW (SEQ ID NO. 68) |

These examples demonstrate the efficacy of the approach to isolating tumor-selective anti-ECM nanobodies targeting tumor-enriched ECM protein epitopes that have been defined by prior proteomic analyses of tumors and metastases. The libraries generated will be a renewable source of multiple other anti-ECM antibodies to other tumor-enhanced ECM epitopes (note that the ECM-enriched preparations used to immunize the alpacas have been analyzed by mass spectrometry so we know the constituent ECM components).

Having thus described several aspects of embodiments of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

---

The invention claimed is:

1. A composition, comprising a nanobody which is specific for and binds directly to a diseased state extracellular matrix (ECM) epitope, wherein the diseased state ECM epitope is (i) an epitope in EIIIB domain of fibronectin, or (ii) tenascin C or an epitope of tenascin C, wherein the nanobody is conjugated to an active agent, and wherein the nanobody comprises a complementarity determining region (CDR)1, CDR2 and CDR3 comprising a) SEQ ID NO: 19, SEQ ID NO: 36, and SEQ ID NO: 53, respectively; b) SEQ ID NO: 25, SEQ ID NO: 42, and SEQ ID NO: 59, respectively; c) SEQ ID NO: 26, SEQ ID NO: 43, and SEQ ID NO: 60, respectively; or d) SEQ ID NO: 28, SEQ ID NO: 45, and SEQ ID NO: 62, respectively.

2. The composition of claim 1, wherein the active agent is linked to N-terminus of the nanobody.

3. The composition of claim 1, wherein the active agent is linked to C-terminus of the nanobody.

4. The composition of claim 1, wherein the active agent is an imaging probe.

5. The composition of claim 4, wherein the imaging probe is selected from the group consisting of: a fluorophore, an immuno-histochemical tracer, a PET tracer, an NIR probe, a SPECT probe, a magnetic particle imaging probe, and a radio-isotope.

6. The composition of claim 1, wherein the active agent is selected from the group consisting of: a drug, a toxin, an siRNA, an shRNA, a cytokine, an ECM remodeling enzyme, a CAR-T cell, a radio-isotope, and a nanoparticle drugs, toxins, siRNAs, shRNAs, cytokines, ECM remodeling enzymes, CAR T cells, and radio isotopes for targeted therapies or can be incorporated into nanoparticles conjugated with the nanobodies for selective delivery.

7. The composition of claim 1, wherein the nanobody specifically binds the diseased state ECM epitope with a binding affinity in a nM to sub-pM range, and wherein the binding affinity is measured by Biolayer Interferometry (BLI).

8. The composition of claim 1, wherein the nanobody comprises a sequence set forth in any one of SEQ ID NOs: 1-4.

9. A composition, comprising
a peptide comprising a sequence set forth in any one of SEQ ID NOs: 1-4 or an antigen-binding fragment thereof and a pharmaceutically acceptable carrier.

10. The composition of claim 9, wherein the peptide is conjugated to an active agent.

11. The composition of claim 9, wherein the peptide is a monoclonal antibody, a humanized antibody, a chimeric antibody, a human antibody, or an antigen-binding fragment thereof.

12. The composition of claim 9, wherein the fragment thereof is a CDR and wherein the peptide comprises a CDR1, CDR2 and CDR3 comprising a sequence having at least 80% sequence identity to a) SEQ ID NO: 19, SEQ ID NO: 36, and SEQ ID NO: 53, respectively; b) SEQ ID NO: 25, SEQ ID NO: 42, and SEQ ID NO: 59, respectively; c) SEQ ID NO: 26, SEQ ID NO: 43, and SEQ ID NO: 60, respectively; or d) SEQ ID NO: 28, SEQ ID NO: 45, and SEQ ID NO: 62, respectively.

13. The composition of claim 9, comprising a nanobody comprising a sequence set forth in any one of SEQ ID NOs: 1-4 or an antigen-binding fragment thereof and a pharmaceutically acceptable carrier.

14. The composition of claim 1, wherein the nanobody specifically binds the diseased state ECM epitope with a binding affinity in a sub-pM range.

15. The composition of claim 1, wherein the nanobody specifically binds the diseased state ECM epitope with a binding affinity in a pM range.

* * * * *

UNITED STATES PATENT AND TRADEMARK OFFICE
CERTIFICATE OF CORRECTION

PATENT NO. : 11,597,769 B2
APPLICATION NO. : 16/258457
DATED : March 7, 2023
INVENTOR(S) : Richard O. Hynes et al.

It is certified that error appears in the above-identified patent and that said Letters Patent is hereby corrected as shown below:

In the Claims

At Column 79, Claim 6, Lines 11-15:
"...a CAR-T cell, a radio-isotope, and a nanoparticle drugs, toxins, siRNAs, shRNAs, cytokines, ECM remodeling enzymes, CAR T cells, and radio isotopes for targeted therapies or can be incorporated into nanoparticles conjugated with the nanobodies for selective delivery."

Should read:
--...a CAR-T cell, a radio-isotope, and a nanoparticle.--

Signed and Sealed this
Sixteenth Day of May, 2023

Katherine Kelly Vidal
*Director of the United States Patent and Trademark Office*

SEQUENCE LISTING

<160> NUMBER OF SEQ ID NOS: 68

<210> SEQ ID NO 1
<211> LENGTH: 133
<212> TYPE: PRT
<213> ORGANISM: Artificial sequence
<220> FEATURE:
<223> OTHER INFORMATION: Synthetic polypeptide

<400> SEQUENCE: 1

Gln Val Gln Leu Val Glu Thr Gly Gly Gly Leu Val Gln Ala Gly Gly
1               5                   10                  15

Ser Leu Arg Leu Ser Cys Ala Ala Ser Gly Ser Thr Phe Ser His Asn
            20                  25                  30

Ala Gly Gly Trp Tyr Arg Gln Ala Pro Glu Lys Gln Arg Glu Leu Val
        35                  40                  45

Ala Gly Ile Ser Ser Asp Gly Asn Ile Asn Tyr Ala Asp Ser Val Lys
    50                  55                  60

Asp Arg Phe Thr Ile Ser Arg Asp Asn Ala Ser Asn Thr Met Tyr Leu
65                  70                  75                  80

Gln Met Asn Asn Leu Lys Pro Glu Asp Thr Ala Val Tyr Val Cys Asn
                85                  90                  95

Ile Arg Gly Ser Tyr Gly Asn Thr Tyr Tyr Ser Arg Trp Gly Gln Gly
            100                 105                 110

Thr Gln Val Thr Val Ser Ser Gly Gly Leu Pro Glu Thr Gly Gly His
        115                 120                 125

His His His His His
    130

<210> SEQ ID NO 2

<211> LENGTH: 138
<212> TYPE: PRT
<213> ORGANISM: Artificial sequence
<220> FEATURE:
<223> OTHER INFORMATION: Synthetic polypeptide

<400> SEQUENCE: 2

Gln Val Gln Leu Val Glu Thr Gly Gly Gly Leu Ala Gln Ala Gly Gly
1               5                   10                  15

Ser Leu Arg Leu Ser Cys Ala Ala Ser Gly Arg Thr Leu Ser Gly Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Arg Asn Thr Tyr Tyr Asp Tyr Thr Val
    50                  55                  60

Gln Gly Arg Phe Thr Ile Ser Lys Asp Asn Ala Lys Asn Thr Val Asn
65                  70                  75                  80

Leu Gln Met Asn Ser Leu Lys Pro Glu Asp Thr Ala Val Tyr Tyr Cys
                85                  90                  95

Ala Val Ser Arg Ser Leu Asp Glu Phe Gly Asp Gly Tyr Glu Met Asp
            100                 105                 110

Tyr Trp Gly Asp Gly Thr Gln Val Thr Val Ser Ser Gly Gly Leu Pro
        115                 120                 125

Glu Thr Gly Gly His His His His His His
    130                 135

<210> SEQ ID NO 3
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Arg Trp Tyr Arg Gln Ala Pro Gly Lys Glu Arg Glu Leu Val
        35                  40                  45

Ala Phe Ile Gly Val Ala Gly Gly Ser Thr Lys Tyr Ala Asp Ser Val
    50                  55                  60

Lys Gly Arg Phe Thr Ile Ser Arg Asp Asn Thr Lys Asn Thr Val Tyr
65                  70                  75                  80

Leu Gln Met Asn Thr Leu Lys Pro Glu Asp Thr Ala Val Tyr Tyr Cys
                85                  90                  95

Tyr Ala Pro Leu Thr Pro Tyr Trp Gly Gln Gly Thr Gln Val Thr Val
            100                 105                 110

Ser Ser Gly Gly Leu Pro Glu Thr Gly Gly His His His His His His
        115                 120                 125

<210> SEQ ID NO 4
<211> LENGTH: 136
<212> TYPE: PRT
<213> ORGANISM: Artificial sequence
<220> FEATURE:
<223> OTHER INFORMATION: Synthetic polypeptide

<400> SEQUENCE: 4

Gln Val Gln Leu Val Glu Thr Gly Gly Asp Leu Val Gln Pro Gly Gly
1               5                   10                  15

Ser Leu Arg Leu Ser Cys Ala Ala Ser Gly Leu Thr Leu Asp Tyr Tyr
            20                  25                  30

Ala Ile Gly Trp Val Arg Gln Ala Pro Gly Lys Glu Arg Glu Gly Val
            35                  40                  45

Ser Cys Ile Thr Pro Gln Asp Gly Asn Thr Tyr Tyr Asp Asp Ser Val
50                  55                  60

Met Gly Arg Phe Thr Ile Leu Arg Asp Asn Ala Lys Asn Met Val Tyr
65                  70                  75                  80

Leu Gln Met Asn Asn Leu Lys Pro Glu Asp Thr Ala Val Tyr Phe Cys
            85                  90                  95

Ala Ala Ala Gly Ala Leu Thr Leu Asp Pro Ser Glu Tyr Glu Tyr Trp
            100                 105                 110

Gly Gln Gly Thr Gln Val Thr Val Ser Ser Gly Gly Leu Pro Glu Thr
            115                 120                 125

Gly Gly His His His His His His
            130                 135

<210> SEQ ID NO 5
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 5

Gln Val Gln Leu Val Glu Thr Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
            35                  40                  45

Ala Ser Ile Ser Arg Gly Gly Thr Thr Ser Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Phe Ala Ser Phe Gly Gly Val Ala Val Val Gly Arg Tyr Trp Gly Gln
            100                 105                 110

Gly Thr Gln Val Thr Val Ser Ser Gly Gly Leu Pro Glu Thr Gly Gly
            115                 120                 125

His His His His His His
    130

<210> SEQ ID NO 6
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 6

Gln Val Gln Leu Val Glu Thr Gly Gly Gly Leu Val Gln Ala Gly Gly
1               5                   10                  15

Ser Leu Arg Leu Ser Cys Glu Val Ser Gly Met Ile Phe Ser Leu Asn
            20                  25                  30

```
Gly Tyr Asn Trp Tyr Arg Gln Ala Pro Gly Asn Gln Arg Glu Leu Val
            35                  40                  45

Ala Gly Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Val Phe Leu
 65                  70                  75                  80

Gln Met Asn Ser Leu Lys Pro Glu Asp Thr Ala Val Tyr Tyr Cys Asn
                 85                  90                  95

Ala Arg Ser Lys Trp Gly Gln Gly Thr Gln Val Thr Val Ser Ser Gly
            100                 105                 110

Gly Leu Pro Glu Thr Gly Gly His His His His His
            115                 120                 125

<210> SEQ ID NO 7
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 7

Gln Val Gln Leu Val Glu Thr Gly Gly Gly Val Val Gln Ala Gly Gly
 1               5                  10                  15

Ser Leu Arg Leu Ser Cys Ala Ala Ser Ala Ser Ile Phe Lys Ile Ile
            20                  25                  30

Thr Met Gly Trp Tyr Arg Gln Ala Pro Gly Lys Gln Arg Glu Ser Val
            35                  40                  45

Ala Thr Ile Thr Arg Gly Gly Asn Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Gly Ala Pro Tyr Val Arg Asn Asn Gly Ser Trp Gly Gln Gly Thr Gln
            100                 105                 110

Val Thr Val Ser Ser Gly Gly Leu Pro Glu Thr Gly Gly His His His
            115                 120                 125

His His His
        130

<210> SEQ ID NO 8
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 8

Gln Val Gln Leu Val Glu Thr Gly Gly Gly Ser Val Gln Ala Gly Gly
 1               5                  10                  15

Ser Leu Arg Leu Ser Cys Ala Ala Ser Leu Asn Ile Phe Arg Leu Tyr
            20                  25                  30

Thr Met Gly Trp Tyr Arg Gln Ala Pro Gly Arg Gln Arg Glu Leu Val
            35                  40                  45

Ala Thr Ile Thr Arg Gly Gly Ser Thr Asn Tyr Ala Asp Ser Val Lys
 50                  55                  60

Gly Arg Phe Thr Ala Ser Arg Asp Asn Thr Lys Asn Thr Val Tyr Leu
```

```
                65                  70                  75                  80
Gln Met Asn Ser Leu Lys Pro Glu Asp Thr Ala Val Tyr Tyr Cys Asn
                85                  90                  95

Arg Asp Leu Lys Leu Gln Pro Trp Val Trp Gly Gln Gly Thr Gln Val
            100                 105                 110

Thr Val Ser Ser Gly Gly Leu Pro Glu Thr Gly Gly His His His His
        115                 120                 125

His His
    130

<210> SEQ ID NO 9
<211> LENGTH: 137
<212> TYPE: PRT
<213> ORGANISM: Artificial sequence
<220> FEATURE:
<223> OTHER INFORMATION: Synthetic polypeptide

<400> SEQUENCE: 9

Gln Val Gln Leu Val Glu Ser Gly Gly Gly Leu Val Gln Ala Gly Asp
1               5                   10                  15

Ser Leu Arg Leu Ser Cys Val Gly Ser Gly Leu Thr Leu Asp Tyr Tyr
            20                  25                  30

Gly Val Gly Trp Phe Arg Gln Ala Pro Gly Lys Glu Arg Glu Gly Val
        35                  40                  45

Ser Cys Ile Ser Arg Ser Asp Gly Ser Thr Tyr Tyr Thr Asp Ser Val
    50                  55                  60

Lys Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Trp Gly Ser Ser Cys Leu Val Glu Asp Phe Gly Ser
            100                 105                 110

Trp Gly Gln Gly Thr Gln Val Thr Val Ser Ser Gly Gly Leu Pro Glu
        115                 120                 125

Thr Gly Gly His His His His His His
    130                 135

<210> SEQ ID NO 10
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 10

Gln Val Gln Leu Val Glu Ser Gly Gly Gly Leu Val Gln Pro Gly Gly
1               5                   10                  15

Ser Leu Arg Leu Ala Cys Thr Leu Ser Gly Phe Thr Ser Gly Ser Tyr
            20                  25                  30

Tyr Met Ser Trp Tyr Arg Gln Ala Pro Gly Lys Glu Arg Gly Phe Val
        35                  40                  45

Ala Arg Ile Phe Ser Ala Gly Gly Ser Thr Asp Tyr Thr Ala Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95
```

```
Asn Ala Arg Gly Tyr Trp Gln Gly Thr Gln Val Thr Val Ser Ser
                100                 105                 110

Gly Gly Leu Pro Glu Thr Gly His His His His His
        115                 120                 125
```

<210> SEQ ID NO 11
<211> LENGTH: 133
<212> TYPE: PRT
<213> ORGANISM: Artificial sequence
<220> FEATURE:
<223> OTHER INFORMATION: Synthetic polypeptide

<400> SEQUENCE: 11

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Ala Met Ser Trp Tyr Arg Gln Ala Pro Gly Lys Gly Arg Glu Leu Val
        35                  40                  45

Ala Ala Ile Thr Ser Thr Gly Gly Ser Thr Asn Tyr Ala Ala Pro Val
    50                  55                  60

Lys Gly Arg Phe Thr Ile Ser Arg Asp Asn Ala Lys Asn Thr Val Leu
65                  70                  75                  80

Leu Gln Met Asn Ser Leu Lys Pro Glu Asp Thr Ala Val Tyr Tyr Cys
                85                  90                  95

His Gln Gly Trp Val Arg Ser Leu Gly Ala Asp Tyr Trp Gly Gln Gly
                100                 105                 110

Thr Gln Val Thr Val Ser Ser Gly Gly Leu Pro Glu Thr Gly Gly His
            115                 120                 125

His His His His His
        130
```

<210> SEQ ID NO 12
<211> LENGTH: 137
<212> TYPE: PRT
<213> ORGANISM: Artificial sequence
<220> FEATURE:
<223> OTHER INFORMATION: Synthetic polypeptide

<400> SEQUENCE: 12

```
Gln Val Gln Leu Val Glu Thr Gly Gly Gly Leu Val Gln Pro Gly Gly
1               5                   10                  15

Ser Leu Arg Leu Ala Cys Thr Leu Ser Gly Phe Thr Ser Gly Ser Tyr
            20                  25                  30

Tyr Met Ser Trp Tyr Arg Gln Ala Pro Gly Lys Glu Arg Gly Phe Val
        35                  40                  45

Ala Arg Ile Phe Ser Ala Gly Ser Thr Asp Tyr Thr Ala Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Gly Asp Thr Gly Val Tyr Tyr Cys
                85                  90                  95

His Ala Thr Val Ser Asp Gln Ile Arg Pro Trp Val Ala Gly Asp Tyr
                100                 105                 110

Trp Gly Gln Gly Thr Gln Val Thr Val Ser Ser Gly Gly Leu Pro Glu
            115                 120                 125

Thr Gly Gly His His His His His His
        130                 135
```

<210> SEQ ID NO 13
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 13

```
Gln Val Gln Leu Val Glu Ser Gly Gly Gly Leu Val Gln Pro Gly Gly
1               5                   10                  15

Ser Leu Arg Leu Ala Cys Thr Ala Ser Gly Phe Arg Val Glu Gly Ser
            20                  25                  30

Ala Ile Gly Trp Phe Arg Gln Ala Pro Gly Lys Gln Arg Asp Leu Val
        35                  40                  45

Ala Ala Ile Thr Arg Arg Gly Thr Thr Thr Tyr Val Asp Ser Val Gln
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Lys Pro Thr Val Ala Arg Ala Tyr Trp Gly Gln Gly Thr Gln Val
            100                 105                 110

Thr Val Ser Ser Gly Gly Leu Pro Glu Thr Gly Gly His His His His
        115                 120                 125

His His
    130
```

<210> SEQ ID NO 14
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 14

```
Gln Val Gln Leu Val Glu Thr Gly Gly Gly Leu Val Gln Pro Gly Gly
1               5                   10                  15

Ser Leu Arg Leu Ser Cys Thr Ala Ser Gly Phe Arg Val Glu Gly Ser
            20                  25                  30

Ala Ile Gly Trp Phe Arg Gln Ala Pro Gly Lys Gln Arg Asp Leu Val
        35                  40                  45

Ala Ala Ile Thr Arg Arg Gly Thr Thr Thr Tyr Val Asp Ser Val Gln
    50                  55                  60

Gly Arg Phe Thr Val Ser Arg Asp Asn Ala Glu Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Lys Pro Thr Val Ala Arg Ala Tyr Trp Gly Gln Gly Thr Gln Val
            100                 105                 110

Thr Val Ser Ser Gly Gly Leu Pro Glu Thr Gly Gly His His His His
        115                 120                 125

His His
    130
```

<210> SEQ ID NO 15
<211> LENGTH: 130
<212> TYPE: PRT

<213> ORGANISM: Artificial sequence
<220> FEATURE:
<223> OTHER INFORMATION: Synthetic polypeptide

<400> SEQUENCE: 15

Gln Val Gln Leu Val Glu Ser Gly Gly Asp Leu Val Gln Pro Gly Gly
1               5                   10                  15

Ser Leu Arg Leu Ser Cys Ala Ala Ser Gly Phe Arg Val Glu Gly Ser
            20                  25                  30

Ala Ile Gly Trp Phe Arg Gln Ala Pro Gly Lys Glu Arg Asp Leu Val
        35                  40                  45

Ala Ala Ile Thr Arg Arg Gly Thr Thr Thr Tyr Val Asp Ser Val Gln
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Lys Pro Thr Val Ala Arg Ala Tyr Trp Gly Gln Gly Thr Gln Val
            100                 105                 110

Thr Val Ser Ser Gly Gly Leu Pro Glu Thr Gly Gly His His His His
        115                 120                 125

His His
    130

<210> SEQ ID NO 16
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 16

Gln Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Ser Trp Tyr Arg Gln Thr Pro Gly Lys Gln Arg Glu Leu Val
        35                  40                  45

Ala Ser Ile Thr Gly Ser Gly Arg Thr Asn Tyr Ala Val Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Arg Lys Asn Leu Leu Leu Gly Ala Phe Thr Trp Gly Gln Gly Thr Gln
            100                 105                 110

Val Thr Val Ser Ser Gly Gly Leu Pro Glu Thr Gly Gly His His His
        115                 120                 125

His His His
    130

<210> SEQ ID NO 17
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 17

Gln Val Gln Leu Val Glu Ser Gly Gly Gly Leu Val Gln Ser Gly Gly
1               5                   10                  15

Ser Leu Arg Leu Ser Cys Thr Ala Ser Gly Phe Val Val Glu Gly Ala
            20                  25                  30

Ala Ile Gly Trp Phe Arg Gln Ala Pro Gly Lys Gln Arg Asp Leu Val
        35                  40                  45

Ala Ala Ile Thr Arg Arg Gly Thr Thr Thr Tyr Val Asp Ser Val Gln
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Lys Pro Thr Val Ala Arg Ala Tyr Trp Gly Gln Gly Thr Gln Val
            100                 105                 110

Thr Val Ser Ser Gly Gly Leu Pro Glu Thr Gly Gly His His His His
        115                 120                 125

His His
    130

<210> SEQ ID NO 18
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 18

Gly Ser Ile Phe Ser Ile Asn Ala Met Gly
1               5                   10

<210> SEQ ID NO 19
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 19

Gly Ser Thr Phe Ser His Asn Ala Gly Gly
1               5                   10

<210> SEQ ID NO 20
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 20

Gly Met Ile Phe Ser Leu Asn Gly Tyr Asn
1               5                   10

<210> SEQ ID NO 21
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 21

Ser Ala Ser Ile Phe Lys Ile Ile Thr Met Gly
1               5                   10

<210> SEQ ID NO 22
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 22

Ser Leu Asn Ile Phe Arg Leu Tyr Thr Met Gly
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 23

Ser Gly Leu Thr Leu Asp Tyr Tyr Gly Val Gly
1               5                   10

<210> SEQ ID NO 24
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 24

Ser Gly Phe Thr Ser Gly Ser Tyr Tyr Met Ser
1               5                   10

<210> SEQ ID NO 25
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 25

Ser Gly Arg Thr Leu Ser Gly Tyr Ala Met Gly
1               5                   10

<210> SEQ ID NO 26
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 26

Ser Gly Phe Thr Phe Ser Ser Tyr Thr Met Arg
1               5                   10

<210> SEQ ID NO 27
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 27

Ser Gly Phe Ala Phe Ser Ser Tyr Ala Met Ser
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 28

Ser Gly Leu Thr Leu Asp Tyr Tyr Ala Ile Gly
1               5                   10

<210> SEQ ID NO 29
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 29

Ser Gly Phe Thr Ser Gly Ser Tyr Tyr Met Ser
1               5                   10

<210> SEQ ID NO 30
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 30

Ser Gly Phe Arg Val Glu Gly Ser Ala Ile Gly
1               5                   10

<210> SEQ ID NO 31
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 31

Ser Gly Phe Arg Val Glu Gly Ser Ala Ile Gly
1               5                   10

<210> SEQ ID NO 32
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 32

Ser Gly Phe Arg Val Glu Gly Ser Ala Ile Gly
1               5                   10

<210> SEQ ID NO 33
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 33

Ser Gly Phe Thr Phe Ser Ser Tyr Ala Met Ser
1               5                   10

```
<210> SEQ ID NO 34
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 34

Ser Gly Phe Val Val Glu Gly Ala Ala Ile Gly
1               5                   10

<210> SEQ ID NO 35
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 35

Ala Ser Ile Ser Arg Gly Gly Thr Thr Ser Tyr Ala Asp
1               5                   10

<210> SEQ ID NO 36
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 36

Ala Gly Ile Ser Ser Asp Gly Asn Ile Asn Tyr Ala Asp
1               5                   10

<210> SEQ ID NO 37
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 37

Ala Gly Ile Thr Arg Gly Gly Ser Thr Asn Tyr Ala Asp
1               5                   10

<210> SEQ ID NO 38
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 38

Ala Thr Ile Thr Arg Gly Gly Asn Thr Asn Tyr Ala Asp
1               5                   10

<210> SEQ ID NO 39
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 39

Ala Thr Ile Thr Arg Gly Gly Ser Thr Asn Tyr Ala Asp
1               5                   10

<210> SEQ ID NO 40
```

```
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 40

Ser Cys Ile Ser Arg Ser Asp Gly Ser Thr Tyr Tyr Thr Asp
1               5                   10

<210> SEQ ID NO 41
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 41

Ala Arg Ile Phe Ser Ala Gly Gly Ser Thr Asp Tyr Thr Ala
1               5                   10

<210> SEQ ID NO 42
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 42

Ala Ala Ile Ser Trp Ser Gly Arg Asn Thr Tyr Tyr Asp Tyr
1               5                   10

<210> SEQ ID NO 43
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 43

Ala Phe Ile Gly Val Ala Gly Gly Ser Thr Lys Tyr Ala Asp
1               5                   10

<210> SEQ ID NO 44
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 44

Ala Ala Ile Thr Ser Thr Gly Gly Ser Thr Asn Tyr Ala Ala
1               5                   10

<210> SEQ ID NO 45
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 45

Ser Cys Ile Thr Pro Gln Asp Gly Asn Thr Tyr Tyr Asp Asp
1               5                   10

<210> SEQ ID NO 46
<211> LENGTH: 14
```

<212> TYPE: PRT
<213> ORGANISM: Artificial sequence
<220> FEATURE:
<223> OTHER INFORMATION: Synthetic polypeptide

<400> SEQUENCE: 46

Ala Arg Ile Phe Ser Ala Gly Gly Ser Thr Asp Tyr Thr Ala
1               5                   10

<210> SEQ ID NO 47
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 47

Ala Ala Ile Thr Arg Arg Gly Thr Thr Thr Tyr Val Asp
1               5                   10

<210> SEQ ID NO 48
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 48

Ala Ala Ile Thr Arg Arg Gly Thr Thr Thr Tyr Val Asp
1               5                   10

<210> SEQ ID NO 49
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 49

Ala Ala Ile Thr Arg Arg Gly Thr Thr Thr Tyr Val Asp
1               5                   10

<210> SEQ ID NO 50
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 50

Ala Ser Ile Thr Gly Ser Gly Arg Thr Asn Tyr Ala Val
1               5                   10

<210> SEQ ID NO 51
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 51

Ala Ala Ile Thr Arg Arg Gly Thr Thr Thr Tyr Val Asp
1               5                   10

<210> SEQ ID NO 52
<211> LENGTH: 16
<212> TYPE: PRT

<213> ORGANISM: Artificial sequence
<220> FEATURE:
<223> OTHER INFORMATION: Synthetic polypeptide

<400> SEQUENCE: 52

Cys Asn Phe Ala Ser Phe Gly Gly Val Ala Val Val Gly Arg Tyr Trp
1               5                   10                  15

<210> SEQ ID NO 53
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 53

Cys Asn Ile Arg Gly Ser Tyr Gly Asn Thr Tyr Tyr Ser Arg Trp
1               5                   10                  15

<210> SEQ ID NO 54
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 54

Cys Asn Ala Arg Ser Lys Trp
1               5

<210> SEQ ID NO 55
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 55

Cys Asn Gly Ala Pro Tyr Val Arg Asn Asn Gly Ser Trp
1               5                   10

<210> SEQ ID NO 56
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 56

Cys Asn Arg Asp Leu Lys Leu Gln Pro Trp Val Trp
1               5                   10

<210> SEQ ID NO 57
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 57

Cys Ala Ala Asp Leu Trp Gly Ser Ser Cys Leu Val Glu Asp Phe Gly
1               5                   10                  15

Ser Trp

<210> SEQ ID NO 58
<211> LENGTH: 7

```
<212> TYPE: PRT
<213> ORGANISM: Artificial sequence
<220> FEATURE:
<223> OTHER INFORMATION: Synthetic polypeptide

<400> SEQUENCE: 58

Cys Asn Ala Arg Gly Tyr Trp
1               5

<210> SEQ ID NO 59
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 59

Cys Ala Val Ser Arg Ser Leu Asp Glu Phe Gly Asp Gly Tyr Glu Met
1               5                   10                  15

Asp Tyr Trp

<210> SEQ ID NO 60
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 60

Cys Tyr Ala Pro Leu Thr Pro Tyr Trp
1               5

<210> SEQ ID NO 61
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 61

Cys His Gln Gly Trp Val Arg Ser Leu Gly Ala Asp Tyr Trp
1               5                   10

<210> SEQ ID NO 62
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 62

Cys Ala Ala Ala Gly Ala Leu Thr Leu Asp Pro Ser Glu Tyr Glu Tyr
1               5                   10                  15

Trp

<210> SEQ ID NO 63
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 63

Cys His Ala Thr Val Ser Asp Gln Ile Arg Pro Trp Val Ala Gly Asp
1               5                   10                  15
```

```
Tyr Trp

<210> SEQ ID NO 64
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 64

Cys Tyr Ala Lys Pro Thr Val Ala Arg Ala Tyr Trp
1               5                   10

<210> SEQ ID NO 65
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 65

Cys Tyr Ala Lys Pro Thr Val Ala Arg Ala Tyr Trp
1               5                   10

<210> SEQ ID NO 66
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 66

Cys Tyr Ala Lys Pro Thr Val Ala Arg Ala Tyr Trp
1               5                   10

<210> SEQ ID NO 67
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 67

Cys Asn Arg Lys Asn Leu Leu Leu Gly Ala Phe Thr Trp
1               5                   10

<210> SEQ ID NO 68
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 68

Cys Tyr Ala Lys Pro Thr Val Ala Arg Ala Tyr Trp
1               5                   10
```